United States Patent
Guevremont, legally incapacitated

(10) Patent No.: US 7,368,709 B2
(45) Date of Patent: May 6, 2008

(54) LOW FIELD MOBILITY SEPARATION OF IONS USING SEGMENTED CYLINDRICAL FAIMS

(75) Inventor: Roger Guevremont, legally incapacitated, Ottawa (CA); by Maria Guevremont, legal representative, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 315 days.

(21) Appl. No.: 11/197,394

(22) Filed: Aug. 5, 2005

(65) Prior Publication Data
US 2006/0027746 A1  Feb. 9, 2006

Related U.S. Application Data

(60) Provisional application No. 60/598,838, filed on Aug. 5, 2004.

(51) Int. Cl.
*B01D 59/44* (2006.01)
*H01J 49/00* (2006.01)

(52) U.S. Cl. .................. 250/282; 250/281; 250/290

(58) Field of Classification Search ............... 250/281, 250/282, 290
See application file for complete search history.

(56) References Cited

U.S. PATENT DOCUMENTS

| | | | |
|---|---|---|---|
| 6,621,077 B1 | 9/2003 | Guevremont et al. | |
| 6,690,004 B2 | 2/2004 | Miller et al. | |
| 6,753,522 B2 | 6/2004 | Guevremont et al. | |
| 6,822,224 B2 | 11/2004 | Guevremont | |
| 6,972,407 B2 * | 12/2005 | Miller et al. | ................. 250/287 |
| 7,019,291 B2 * | 3/2006 | Miller et al. | ................. 250/292 |
| 7,030,372 B2 * | 4/2006 | Miller et al. | ................. 250/287 |
| 7,057,166 B2 * | 6/2006 | Guevremont et al. | ....... 250/282 |
| 7,075,068 B2 * | 7/2006 | Miller et al. | ................. 250/290 |
| 7,091,481 B2 * | 8/2006 | Miller et al. | ................. 250/288 |
| 7,098,449 B1 * | 8/2006 | Miller et al. | ................. 250/287 |
| 7,148,477 B2 * | 12/2006 | Miller et al. | ................. 250/294 |
| 7,164,122 B2 * | 1/2007 | Fuhrer et al. | ................ 250/287 |

(Continued)

FOREIGN PATENT DOCUMENTS

CA  2475555  8/2003

(Continued)

*Primary Examiner*—David Vanore
(74) *Attorney, Agent, or Firm*—Freedman & Associates

(57) ABSTRACT

A method of separating ions is disclosed. The method includes a step of providing a FAIMS analyzer region for separating ions, the FAIMS analyzer region including at least one region of segmentation. The segmentation permits ion trapping, and a combination trapping and gating that permits high efficiency of ions collection from continuous ion sources. The ions are separated in segmented FAIMS, according to their high-field mobility properties, and by using the method described herein according to their low-field mobility. The ions are separated by low field mobility using stationary potential gradients formed by voltages applied to the segments, and by traveling potential gradients of various shapes. The ions are separated along the longitudinal direction in cylindrical FAIMS, and may be detected in a time-of-arrival fashion as the ions leave the ion outlet of FAIMS or optionally the ions other than selected are caused to collide with the electrodes and only the selected ions transmitted. This is a high resolution separation, combining the ion properties at high-field, as well as the low-field mobility properties, for selection of specific ions from very complex mixtures.

31 Claims, 27 Drawing Sheets

U.S. PATENT DOCUMENTS

| | | | |
|---|---|---|---|
| 7,170,053 B2 * | 1/2007 | Shvartsburg et al. | 250/287 |
| 7,176,453 B2 * | 2/2007 | Miller et al. | 250/287 |
| 7,211,791 B2 * | 5/2007 | Miller et al. | 250/286 |
| 7,217,920 B2 * | 5/2007 | Miller et al. | 250/287 |
| 7,227,134 B2 * | 6/2007 | Miller et al. | 250/288 |
| 7,230,238 B2 * | 6/2007 | Miller et al. | 250/293 |
| 7,241,989 B2 * | 7/2007 | Miller et al. | 250/282 |
| 7,285,774 B2 | 10/2007 | Guevremont | |
| 2003/0089847 A1 | 5/2003 | Guevremont et al. | |
| 2004/0004185 A9 | 1/2004 | Guevremont et al. | |
| 2004/0240843 A1 | 12/2004 | Miller et al. | |
| 2005/0127284 A1 | 6/2005 | Guevremont et al. | |

FOREIGN PATENT DOCUMENTS

| | | |
|---|---|---|
| WO | WO 2005/067582 | 7/2005 |
| WO | WO 2006/084363 A1 | 8/2006 |
| WO | WO 2006/086880 A1 | 8/2006 |

\* cited by examiner

LOW FIELD MOBILITY SEPARATION OF IONS USING SEGMENTED CYLINDRICAL FAIMS

This application claims benefit from U.S. Provisional Application No. 60/598,838 filed Aug. 05, 2004, the entire contents of which are incorporated herein by reference.

FIELD OF THE INVENTION

The instant invention relates generally to High Field Asymmetric Waveform Ion Mobility Spectrometry (FAIMS). In particular, the instant invention relates to methods and apparatus for high-resolution separation of ions based on their high-field and low-field mobility properties.

BACKGROUND

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994), the contents of which are incorporated herein by reference. In IMS, gas-phase ion mobilities are determined using a drift tube with a constant electric field. Ions are separated in the drift tube on the basis of differences in their drift velocities. At low electric field strength, for example 200 V/cm at approximately ambient atmospheric pressure, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location.

E. A. Mason and E. W. McDaniel in their book entitled "Transport Properties of Ions in Gases" (Wiley, N.Y. 1988), the contents of which are incorporated herein by reference, teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually is neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Numerous ionization sources, including atmospheric pressure ionization sources, have been described for use with FAIMS. Non-limiting examples include electrospray ionization and variants thereof, thermospray, atmospheric pressure chemical ionization, corona discharge, radioactive sources (including $^{63}$Ni and other nuclides). As some non-limiting examples, ions are detected using electrometers for measuring electric current from discharge of the ions, detected by measurement of currents induced by the presence of the ions, detected indirectly using chemical reactions, detected using optical methods such as laser scattering or optical fluoresence. In addition, detection of ions using a mass spectrometer is known.

A typical analytical system that includes FAIMS may include several devices operating in a cooperative manner. For example a sample may be prepared in automated fashion in a commercial robotic station, and transferred to an automatic sampling instrument. This autosampler provides portions of the sample to a separation device that includes gas chromatography or liquid chromatography or electrophoresis as some non-limiting examples of condensed or gas-phase separations. The compounds separated by this system may then be presented to an ionization device to convert the molecules of interest into their respective ions. This change of state of the analyte compound forms the junction between separations of molecules from separations of ions. The ions produced by this ionization system that may be one of electrospray ionization, optical ionization, MALDI ionization, corona discharge ionization, chemical ionization, and radioactive decay as some non-limiting examples, are then presented to a conventional ion mobility spectrometer or to FAIMS, or to a system composed of a hybridization of these methods. Previous disclosures have described some of these, including a tandem FAIMS-IMS system in WO 01/69221 published Sep. 20, 2001, the contents of which are incorporated herein by reference, and a tandem FAIMS-ion trapping system in U.S. Pat. No. 6,703,609, the contents of which are incorporated herein by reference. The FAIMS and drift ion mobility measurements may be made in tandem-in-space instruments or in tandem-in-time operations that may be within a single or a plurality of chambers designed for optimum performance of drift tube or FAIMS versions of high-pressure ion separation. The ions which have been separated by the drift tube, or FAIMS, or hybrid technology is then presented to one of a further separation, or a detection system. Several detection systems have been used including using electrometers for measuring electric current from discharge of the ions, measurement of currents induced by the presence of the ions, indirectly detected using chemical reactions, or detected using optical methods such as laser scattering or optical fluoresence as some non-limiting examples. If further separation is required, ions may be separated by mass spectrometers including one of quadrupole mass spectrometers, ion trap mass spectrometers, and Fourier Transform (FT) ion cyclotron mass spectrometers as some non-limiting examples.

SUMMARY

It is an object of at least some embodiments of the instant invention to simplify the instrumental system relative to tandem-in-space systems in which ions that are separated by FAIMS are coupled into the inlet of a conventional drift tube ion mobility spectrometer.

It is an object of at least some embodiments of the instant invention to combine the separations relating to a FAIMS device and to a conventional drift tube ion mobility spectrometer into one instrument. Accordingly, at least some embodiments of the instant invention support ion separations based on both the low-field ion mobility properties of an ion and the difference of mobility properties of an ion at high-field and at low-field strength conditions. Typically, these two properties are not related one to the other, and therefore the separation of ions based on both ionic properties is expected to yield superior specificity compared to either one taken alone.

It is an object of at least some embodiments of the instant invention to separate ions along the longitudinal direction in segmented FAIMS in dependence upon ion low-field mobility.

Separation of complex mixtures of compounds requires a tandem separation scheme that achieves separation of chemical constituents on the basis of several of their physical and chemical properties. Complex mixtures originating from biological systems usually have significant numbers of related chemical constituents, and separating one compound from the mixture is a problem that is very difficult to resolve. At least some embodiments of the instant invention employ a cylindrical geometry FAIMS that is segmented so to provide independent electrical conditions to each segment along the longitudinal axis of the device. The ions are transported through the device by a combination of gas flows and the electrical field that is generated by consecutive segments being at differing applied voltages. It is an object of at least some embodiments of the instant invention to obtain separation-in-space of the ions in the longitudinal direction along FAIMS in dependence upon their low-field mobility by using static and time-varying applied voltages to the segments of a segmented version of FAIMS.

According to an aspect of the instant invention, there is provided a method of separating ions, comprising: providing a segmented analyzer region having an average ion flow path; during a period of time, providing within the analyzer region an electrical field component that is directed along a direction normal to the average ion flow path, for selectively transmitting within the analyzer region ions having predetermined high field mobility properties; and, during the period of time, providing within the segmented analyzer region an electrical field component that is directed approximately along the average ion flow path, for at least partially separating the selectively transmitted ions in space along the average ion flow path in dependence upon the low field mobility properties of the selectively transmitted ions.

According to another aspect of the instant invention, there is provided a method of separating ions, comprising: providing an analyzer region having an average ion flow path, the analyzer region defined by a space between facing electrode surfaces of a plurality of electrode segment pairs; introducing ions from an ionization source into the analyzer region; applying an asymmetric waveform voltage to at least one electrode segment of each of the plurality of electrode segment pairs and applying a direct current voltage difference between the facing electrode surfaces of each electrode segment pair, to establish an electrical field for selectively transmitting within the analyzer region a subset of the ions having predetermined high field mobility properties; applying a direct current voltage difference between adjacent electrode segment pairs of the plurality of electrode segment pairs, to establish an electric field along the average ion flow path for at least partially separating the subset of the ions in space along the average ion flow path in dependence upon the low field mobility properties of the subset of the ions; and, changing the direct current voltage difference that is applied between the facing electrode surfaces of some of the electrode segment pairs to a value that is not suitable for selectively transmitting ions within the analyzer region between the facing electrode surfaces of the some of the electrode segment pairs, so as to preferentially transmit a type of ion having predetermined high field and low field mobility properties.

According to another aspect of the instant invention, there is provided a method of separating ions, comprising: providing a segmented analyzer region having an average ion flow path; during a period of time, providing within the segmented analyzer region an electrical field component that is directed along a direction normal to the average ion flow path, for selectively transmitting within the segmented analyzer region ions having predetermined high field mobility properties; and, during the period of time, providing within the segmented analyzer region an electrical field component that is directed along the average ion flow path and having an electrical field strength that varies along the average ion flow path, for at least partially separating the selectively transmitted ions in space along the average ion flow path in dependence upon the low field mobility properties of the selectively transmitted ions.

According to another aspect of the instant invention, there is provided a method of separating ions, comprising: providing an analyzer region having an average ion flow path, the analyzer region defined by a space between facing electrode surfaces of a plurality of electrode segment pairs including n segment pairs; during a period of time, applying an asymmetric waveform voltage to each electrode segment pair of the plurality of electrode segment pairs and applying a direct current voltage difference between the facing electrode surfaces of each electrode segment pair, to establish an electrical field for selectively transmitting within the analyzer region a subset of the ions having predetermined high field mobility properties; during a first portion of the period of time, applying to each electrode segment pair a different dc bias voltage relative to a reference voltage, such that in a direction taken along the average ion flow path the applied dc bias voltage one of increases and decreases from one electrode segment pair to an adjacent electrode segment pair between a first electrode segment pair and the $n^{th}$ electrode segment pair; and, during a second portion of the period of time not overlapping the first portion, applying to each electrode segment pair a dc bias voltage corresponding to a dc bias voltage that was applied to an adjacent electrode segment pair during the first portion of the period of time, wherein the application of dc bias voltages during the first portion of the period of time and during the second portion of the period of time cooperate to form a dc bias voltage wavefront that translates along the length of the analyzer region, and wherein the selectively transmitted ions are at least partially separated in space along the wavefront in dependence upon their low field mobility properties.

BRIEF DESCRIPTION OF THE DRAWINGS

Exemplary embodiments of the invention will now be described in conjunction with the following drawings, in which similar reference numerals designate similar items.

DESCRIPTION OF EMBODIMENTS OF THE INSTANT INVENTION

Figure 1:
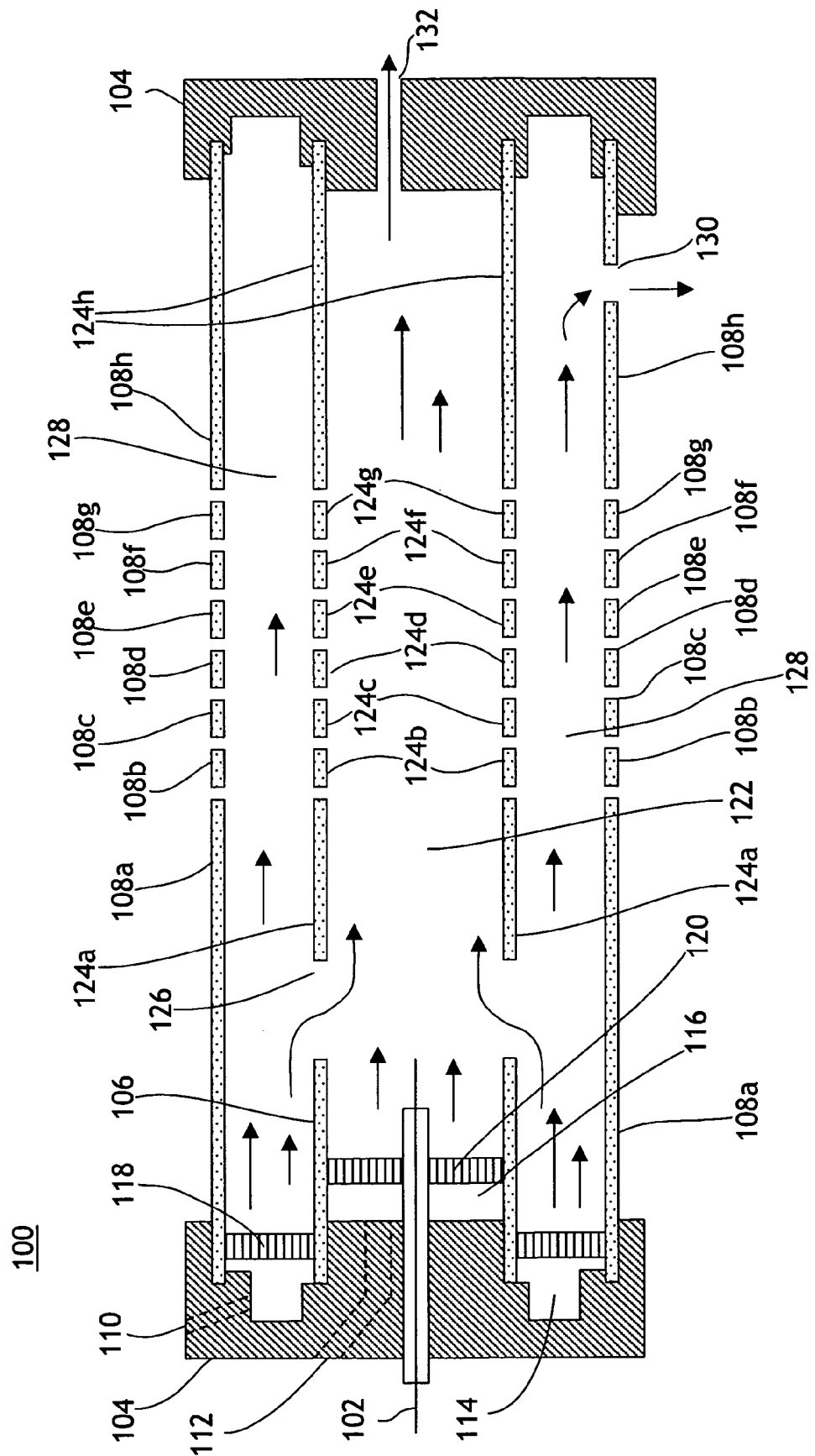
FIG. 1 is a simplified cross-sectional view of a cylindrical geometry FAIMS according to an embodiment of the instant invention.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout much of the following discussion it is assumed that the FAIMS electrodes are operating at atmospheric pressure, but the discussion below is equally applicable at pressures below ambient atmospheric pressure and at pressures exceeding ambient atmospheric pressure conditions. Throughout the detailed description and in the appended claims, the pressures that are suitable for FAIMS will be termed "high pressure" whereas those pressures that are more suitable for mass-to-charge (m/z) measurements using mass spectrometry will be termed "low pressure". For clarity, in some cases certain parts of a mass spectrometer, such as the collision cell for ion dissociation, may be operated at "high pressure" using the definition above, whereas for most instruments the actual separation of ions as a function of their m/z ratio takes place at "low pressure", again using the definition noted above. The term "average ion flow path" is defined as the net trajectory of an ion through the analyzer region, although the individual ion also experiences an oscillatory motion between the electrodes as a result of the applied asymmetric waveform voltage.

Because ion separation and ion transmission in the FAIMS system is susceptible to changes in temperature and gas pressure, it is desirable to operate at selected temperature and pressure conditions. For example, a rise in temperature leads to a decrease in the number density of the gas (N, molecules per cc) and therefore the operating electric field (E/N) increases. Similarly an increase in gas pressure increases N and therefore decrease the effective E/N conditions. In order that experiments give consistent results when repeated, the temperatures and pressures are operated at selected conditions within selected tolerance limits.

It is beneficial that the physical conditions in the analyzer region of FAIMS do not significantly change the CV of the transmission of the ion of interest, while it is passing through the analyzer region, to a degree that may prevent the transmission of the ion of interest. For example, if the conditions differ substantially as the ions are carried through FAIMS, those ions that are initially being successfully transmitted near the ion inlet region, may be lost to the electrode walls at a later time during their passage through the FAIMS analyzer region. This may occur if the conditions near the inlet are in a balanced condition for the selected ion, and the ion is being transmitted near the inlet, but at a location elsewhere in the analyzer region the conditions are sufficiently different that the same ion is migrating to the electrode walls and is being lost. Temperature, pressure and spacing between the electrodes, are among the physical conditions, assuming constant applied voltages, that can affect the CV of transmission of an ion. For example, a substantial difference in the electrode spacing near the ion inlet and near the ion outlet causes the field E/N near the inlet to be different from the field E/N near the outlet. In some cases moderate changes beneficially improve ion separation, but large changes that ions experiences for longer times may result in complete loss of ion transmission. Additionally, the physical conditions may beneficially be varied in specific locations within the FAIMS analyzer region, for example the field E/N may be stronger near the inner electrode than near the outer electrode, and these local variations can be beneficial so long as the overall conditions are not sufficiently changed so as to result in complete loss of the ions. The magnitude of the total changes in physical conditions, and of the local changes in physical conditions, is established by experimental measurements, and the conditions adjusted to achieve the ion transmission sensitivity and the ion separation required.

FIG. 1 is a simplified cross-sectional view of a cylindrical geometry FAIMS according to an embodiment of the instant invention. The cylindrical geometry FAIMS 100 includes a segmented inner electrode 124 including segments 124a to 124h and an outer electrode 108 including segments 108a to 108h. Short segments 124b to 124g are spaced apart from similar length segments 108b to 108g. Ions are produced by ionizer 102 which may include electrospray ionization, corona discharge, atmospheric pressure chemical ionization as some non-limiting examples. The ionizer 102 is mounted in an insulating member 104 that also serves to support a short inner cylinder 106 and a long outer cylinder 108 in a spaced-apart arrangement. A flow of carrier gas passes through a passageway 110 shown by dashed lines in insulating member 104, and a flow of sampler gas flows through passageway 112 shown by dashed lines in insulating member 104. The carrier gas enters a pressure equalization chamber 114, and the sampler gas enters a second equalization chamber 116. Diffusers 118 and 120 serve to restrict the carrier gas flow and the sampler gas flow, respectively, and to allow these gases to flow uniformly around the circumference of the electrodes. The carrier gas passes through the diffuser 118, and flows in a smooth laminar flow along the annular space between the short inner cylinder 106 and the long outer cylinder 108. Similarly the sampler gas passes through the diffuser 120, and flows in a smooth laminar flow along the annular space between the ionizer 102 and the short inner cylinder 106. The sampler gas flows through the inner passage 122 within the inner electrode 124.

Still referring to FIG. 1, the ions produced by ionization source 102 are accelerated away from the source 102 in an outwardly radial direction by a voltage difference between the ionization source 102 and the short inner cylinder 106. Some ions pass through a gap 126 between the short inner cylinder 106 and the first segment 124*a* of the inner cylinder. Those ions that pass through the gap 126 are entrained by the carrier gas and carried along the analyzer region 128, which is the annular space between the inner cylinder 124 and the long outer cylinder 108. The ions for which the applied waveform voltage and the compensation voltage are appropriate, pass through the analyzer region 128, and are carried by the carrier gas out of the FAIMS 100 through ion outlet 130. The ions may be further analyzed by mass spectrometry, and/or other types of ion mobility spectrometers, and/or additional FAIMS devices, and/or may be detected using ion detection technologies including amperometric or photometric as some non-limiting examples.

Still referring to FIG. 1, an asymmetric waveform and compensation voltage is applied to the inner electrode 124. Bias voltages are applied to the short inner electrode 106 and the long outer electrode 108. The segments that comprise the inner electrode 124 and the long outer electrode 108 may be at the same potential, or preferably may be at potentials that permit measurement of the low-field mobility of the ions that are successfully transmitted at the asymmetric waveform voltage and the compensation voltage under the ambient conditions of gas composition, gas pressure, and gas temperature.

Still referring to FIG. 1, it is preferable that a portion of the carrier gas that flows into the passageway 110 and through diffuser 118 enters the inner passage 122 within the inner electrode 124 by flowing radially inward through the gap 126. This inward flow of carrier gas helps to desolvate ions from ionization source 102 that are flowing outward through gap 126. This countercurrent of flowing gas helps to desolvate the ions and also prevents neutrals coming from the ionization source from entering the analyzer region 128. The neutrals produced from the sample, but not ionized by the ionizer 102, flow with the sampler gas along the inner passage 122 within the inner electrode 124 and out of sample outlet port 132. Preferably a gas pump (not shown) assists in pulling the sampler gas out of port 132, and assists in pulling a desolvating portion of carrier gas inward radially through the gap 126.

Still referring to FIG. 1, the number of segments of the inner electrode 124 and of the outer electrode 108 may be larger or fewer than shown in this figure. Further discussions will assume that the electrodes are divided into a large number of segments. The cylindrical arrangement of the inner and outer coaxially arranged electrodes shown in FIG. 1 gives rise to an ion focusing effect within the annular analyzer region between the inner and outer electrodes, for an ion being transmitted at the selected asymmetric waveform (DV) and the selected compensation voltage (CV). This focusing helps to prevent ions from colliding with the inner and outer electrodes. The application of differing bias voltages on the segments of the segmented FAIMS shown in FIG. 1 makes it possible to evaluate the low-field mobility of these ions, in an experiment conducted within an apparatus of the type shown in FIG. 1. Ions are therefore selected on the basis of their high-field mobility behavior, to pass through FAIMS at the selected DV and CV, as well as by their low-field mobility as selected by appropriate voltages and arrangements of voltages applied to the segments of the inner and outer electrodes.

Figure 2A:
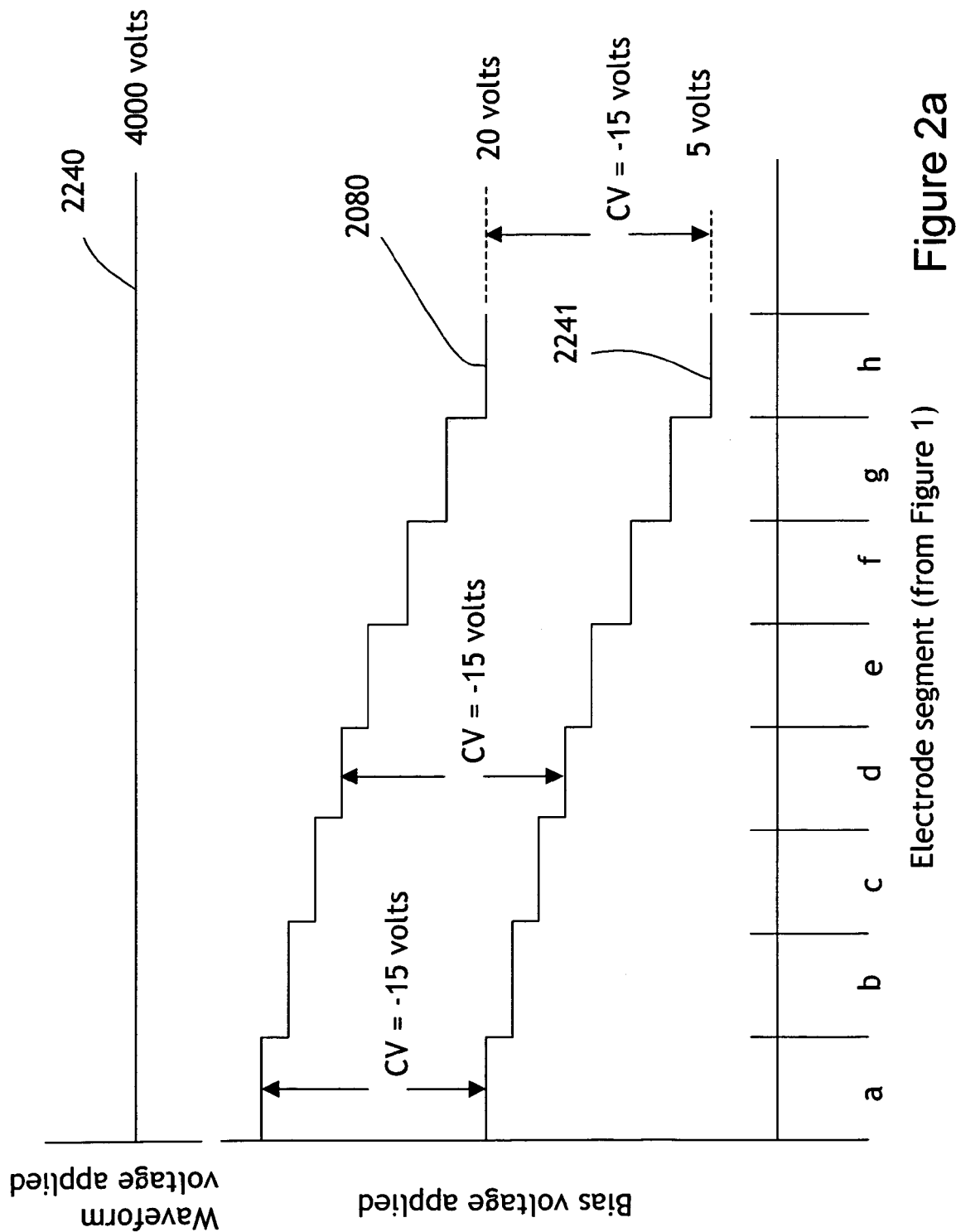
FIG. 2a is a graph of the waveform voltage (DV) and dc bias voltages applied in decreasing steps to the segmented inner and segmented outer electrodes of a segmented FAIMS.

FIG. 2*a* illustrates the voltages applied to the electrodes shown in FIG. 1, in one possible mode of operation. The upper axes of FIG. 2*a* show trace 2240, which is the waveform voltage that is applied to each of the electrode segments 124*a* to 124*h*. Trace 2240 is uniform across all of the segments of inner electrode 124, and the figure shows that 4000 volts of asymmetric waveform is applied equally to all of the segments 124*a* to 124*h*. The lower axes show a trace 2080 that illustrates the dc bias voltage that is applied to the segments of the outer electrode 108 and trace 2241 that shows the bias voltages applied to the segments of inner electrode 124. From the traces 2080 and 2241 it is shown that the voltages differ from segment to segment. The first left-hand edge portion of the traces 2080 and 2241 represent the dc bias voltages applied to the segments 108*a* and 124*a* respectively. Segment 108*a* is shown to be 15 volts higher than segment 124*a*. The subsequent segments 108*b* and 124*b* are both lower that 108*a* and 124*a*, but once again the difference between 108*b* and 124*b* is 15 volts. The difference between the inner and outer electrodes, the compensation voltage CV, is uniform between the inner and outer electrodes at every segment. This is required if the ion of interest is to pass through the analyzer region. However, in this case, each successive segment pair is at a voltage slightly lower than the previous adjacent segment, and the ions are therefore being pulled along the electrode in a direction from "segment a" towards "segment h", from left to right in FIG. 2*a*. Since this is the same direction as the carrier gas flow shown in FIG. 1, the ions traverse the analyzer region more quickly than they would have, absent the voltage gradient established using the electrode segments. It is clear that by reversing the direction of the electrode-to-electrode voltage changes, as shown in FIG. 2*b*, the time that ions require to traverse the analyzer region is lengthened.

Figure 2B:
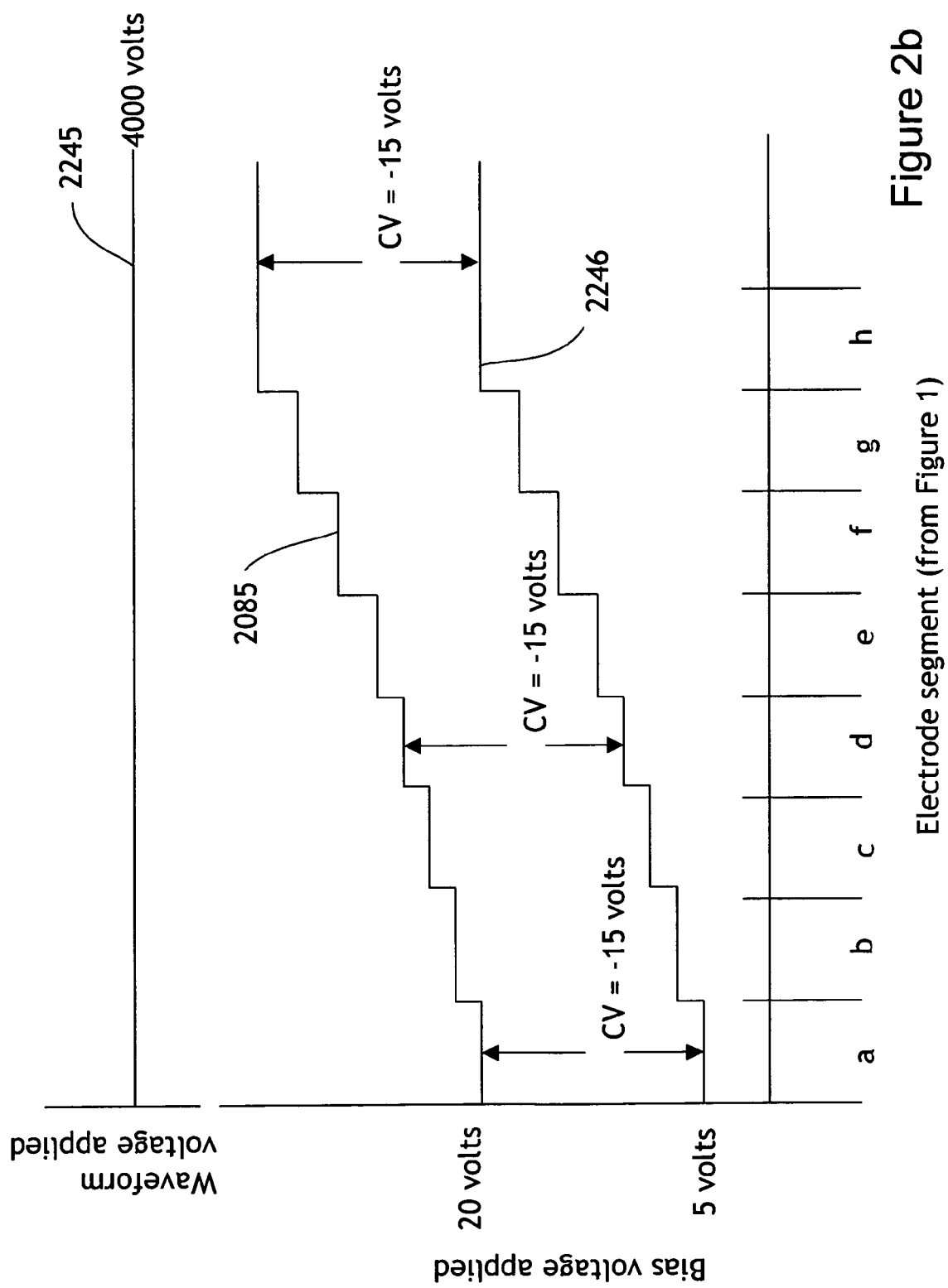
FIG. 2b is a graph of the waveform voltage (DV) and dc bias voltages applied as a series of increasing steps to the segmented inner and segmented outer electrodes of a segmented FAIMS.

Still referring to FIG. 2*b*, the longitudinal electric field gradient created by the voltages applied to the segmented FAIMS is acting in a direction that is in opposition to the flow of carrier gas. At one extreme of a very high gradient, the ions flow in a direction completely against the flow of carrier gas, but in the case of the apparatus shown in FIG. 1, this only prevents the ions from source 102 from reaching the ion outlet 130. At a less steep voltage gradient in the longitudinal direction, the ions reach an equilibrium balance of electric field against the flow of carrier gas. At this condition, absent a flow of carrier gas, the velocity of the ion resulting from the electrode-segment produced longitudinal electric field gradient is a product of the longitudinal field gradient ($E_L$) and the mobility of the ion ($K_e$). The velocity of the ion is equal to the velocity of the carrier gas ($V_c$) absent a longitudinal electric field gradient. At equilibrium, these velocities are equal and $V_c$ equals $E_L K_e$. Ions that have mobility exceeding $K_e$ travel faster than the carrier gas in response to the longitudinal electric field, and those ions with mobility smaller than $K_e$ travel more slowly in response to the longitudinal electric field and therefore can be carried by the gas to the ion exit. By adjustment of the voltage differences between segments, the longitudinal field gradient is adjustable to match various values of mobility $K_e$. The longitudinal voltage gradient, of the type shown in FIG. 2b, resisting the flow of the carrier gas is therefore an ion mobility filter, responding to the low-field mobility of the ions being transported at the conditions of DV, CV and ambient conditions of gas mixture, gas pressure and gas temperature. A scan of the mobilities of these ions is obtained by stepwise modification of the voltages between the adjacent segments shown in FIG. 2b. Clearly, the voltage difference between longitudinally paired segments 108a and 124a, and between 108b and 124b, and so on, of FIG. 1 preferably remains equal to the CV for transmission of a selected ion. The apparatus shown in FIG. 1 therefore produces ion selection simultaneously on the basis of the FAIMS ion separation and the low-field mobility of the FAIMS selected ions.

Figure 3:
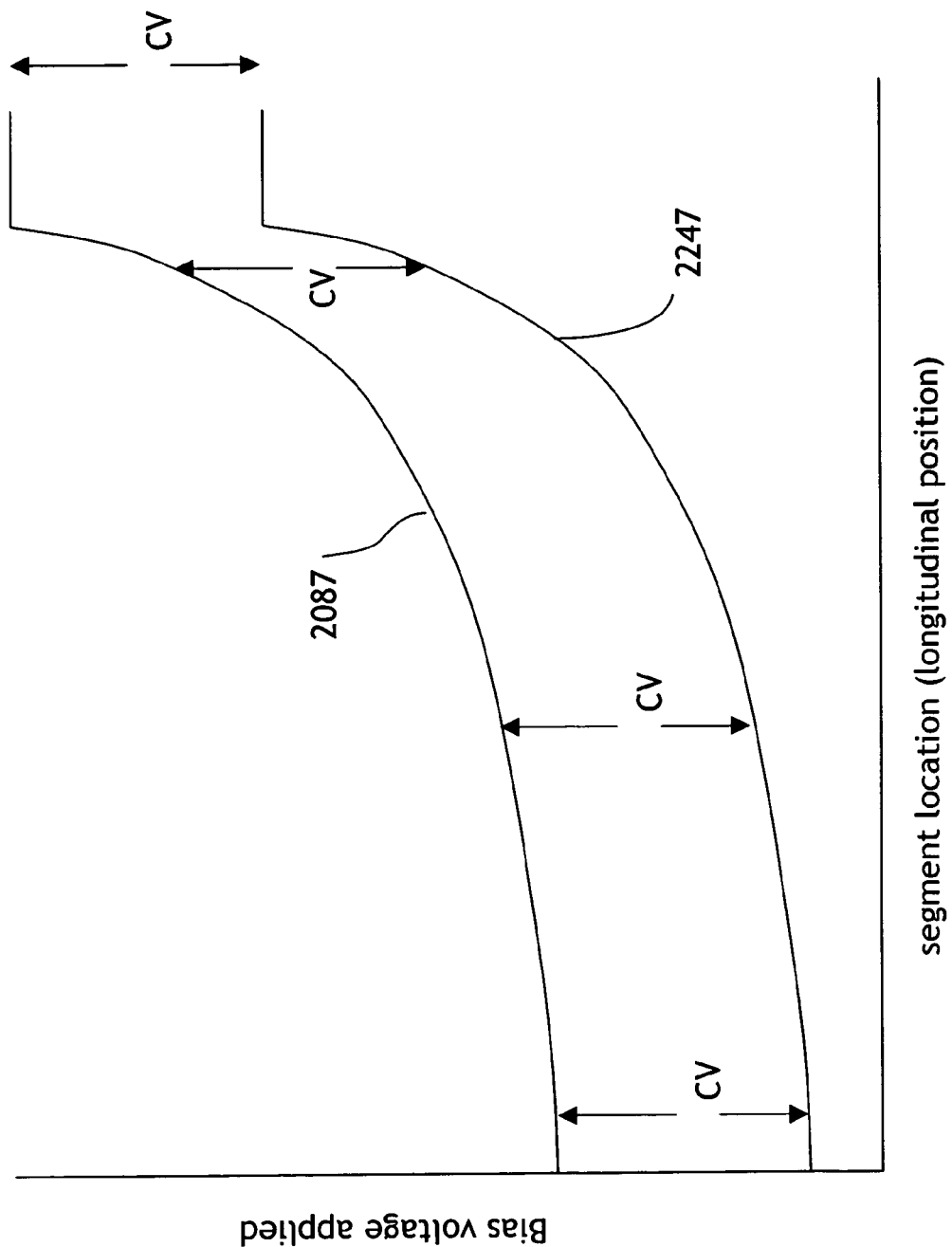
FIG. 3 is a graph of a selected pattern of the dc bias voltages applied to the segmented inner and segmented outer electrodes of a segmented FAIMS.

FIG. 3 illustrates another variation of the voltages that may be applied to the series of adjacent segments of the segmented electrodes 108 and 124 of FIG. 1. In FIG. 3, it is assumed that the electrodes are segmented into a plurality of segments, the longitudinal location of the segments represented by the position along the x-axis and the voltages applied indicated by position along the y-axis. The asymmetric waveform is applied equally to all of the segments of the inner electrode 124 of FIG. 1, and the trace is not shown in FIG. 3. The dc bias voltage difference between a given inner electrode segment and the segment of the outer electrode that is at the same longitudinal location remains equal to the CV. Selection of ions based on the FAIMS separation principle is controlled by conditions of voltage, including the DV and CV, as well as by ambient conditions of carrier gas composition, gas pressure and gas temperature as some non-limiting examples.

Still referring to FIG. 3, the dc bias voltages applied to the inner electrode 124 of FIG. 1 is shown as trace 2247, and the dc bias voltages applied to the segments of outer electrode 108 of FIG. 1 is shown as trace 2087. The dc voltage difference between segments at the same longitudinal position selected to allow passage of an ion of interest through the FAIMS electrodes, and is preferably fixed to be equal to CV. The dc bias of the series of segments shown in FIG. 3 increases in a curve similar to a quadratic function. At each location in the longitudinal direction along the electrodes the electric field in the longitudinal direction is equivalent to the slope of the curves 2247 and 2087. This slope represents the strength of the longitudinal electric field, and therefore represents the force applied to an ion in this longitudinal direction. An ion moves fastest in the longitudinal direction in the region of high slope of curves 2247 and 2087, and more slowly in regions of lower slope. Since a flow of carrier gas moves along the analyzer region 128 of FIG. 1, this adds a velocity component to the ions, also aligned in the longitudinal direction. Absent a gradient shown by curves 2247 and 2087, the ion drifts along the analyzer region 128 at velocity equal to the gas flow velocity. The ion velocity imposed by the longitudinal fields generated by applying voltages shown by curves 2247 and 2087 is then superimposed upon the gas flow velocity.

Still referring to FIG. 3, the ions experience a force due to the electric field that increases along the length of the segmented sections of electrodes 124 and 108 of FIG. 1. The velocity of an ion that results from this electric field is increasing, and is approximately proportional to the low field mobility of the ion. In combination with the flow of carrier gas along the analyzer region 128 of FIG. 1, the electric fields generated in the longitudinal direction by voltages applied as shown in FIG. 3, act to separate a mixture of ions according to the value of their low-field ion mobility. Ions with high mobility reach an equilibrium balance between the carrier gas velocity and the velocity generated by the longitudinal electric field at a region of low longitudinal field, shown near the left portion of the curves 2247 and 2087. Similarly, ions with low mobility reach an equilibrium balance, that is to say zero net velocity in the longitudinal direction, along a steeper portion of the curves 2247 and 2087. The mixture of ions, all of which must have high-field mobility behavior according to applied DV and CV conditions, is separated along the longitudinal direction within the analyzer region of FAIMS, the higher mobility ions located in regions of lower longitudinal field strength and lower mobility ions similarly located at regions of higher longitudinal field strength. Because of the focusing action of FAIMS in a cylindrical geometry, the ions are generally located in the center of the analyzer region, the focusing action minimizing collisions of the ions with the electrode surfaces. During application of the voltages shown by traces 2247 and 2087 of FIG. 3, only ions with a limit of low mobility reach the ion exit 130 shown in FIG. 1. The other ions accumulate along the analyzer region, their longitudinal position related to their low field ion mobility. A read-out of this profile occurs if the voltages on the segments are replaced with constant voltages, thereby releasing the ions to be carried by the carrier flow out of ion exit 130. The arrival time of each ion is indicative of the low-field mobility of the ion.

Still referring to FIG. 3, after a mixture of ions has been separated, firstly because of the applied FAIMS conditions of CV and DV, and secondly in the longitudinal direction as a function of low-field ion mobility, the voltages shown in FIG. 3 can be gradually reduced and reducing the longitudinal field strength so that the ions are released, or extracted, gradually over time, each extracted in a sequence representative of their low field mobility. During this ion extraction process it is advantageous that no further mixture of ions arrive in the analyzer, because this new mixture would not yet be separated longitudinally in space, as described above.

As discussed above in relation to FIG. 3, the voltages on the segments of the segmented inner and outer electrodes need not remain constant in time. The ions can be released to flow along with the carrier gas by making all of the segments at equal voltage. The ions can be made to travel in longitudinal directions either in the direction of the carrier gas flow, or in a direction contrary to the carrier gas flow. In some cases this latter condition is preferable for maintaining the preselected composition of the carrier gas, avoiding introduction of neutrals from the ionization process. It is common in conventional drift tube ion mobility of the time-of-flight type that the bath gas flows in a direction contrary to the direction of the ion drift.

Figure 4A:
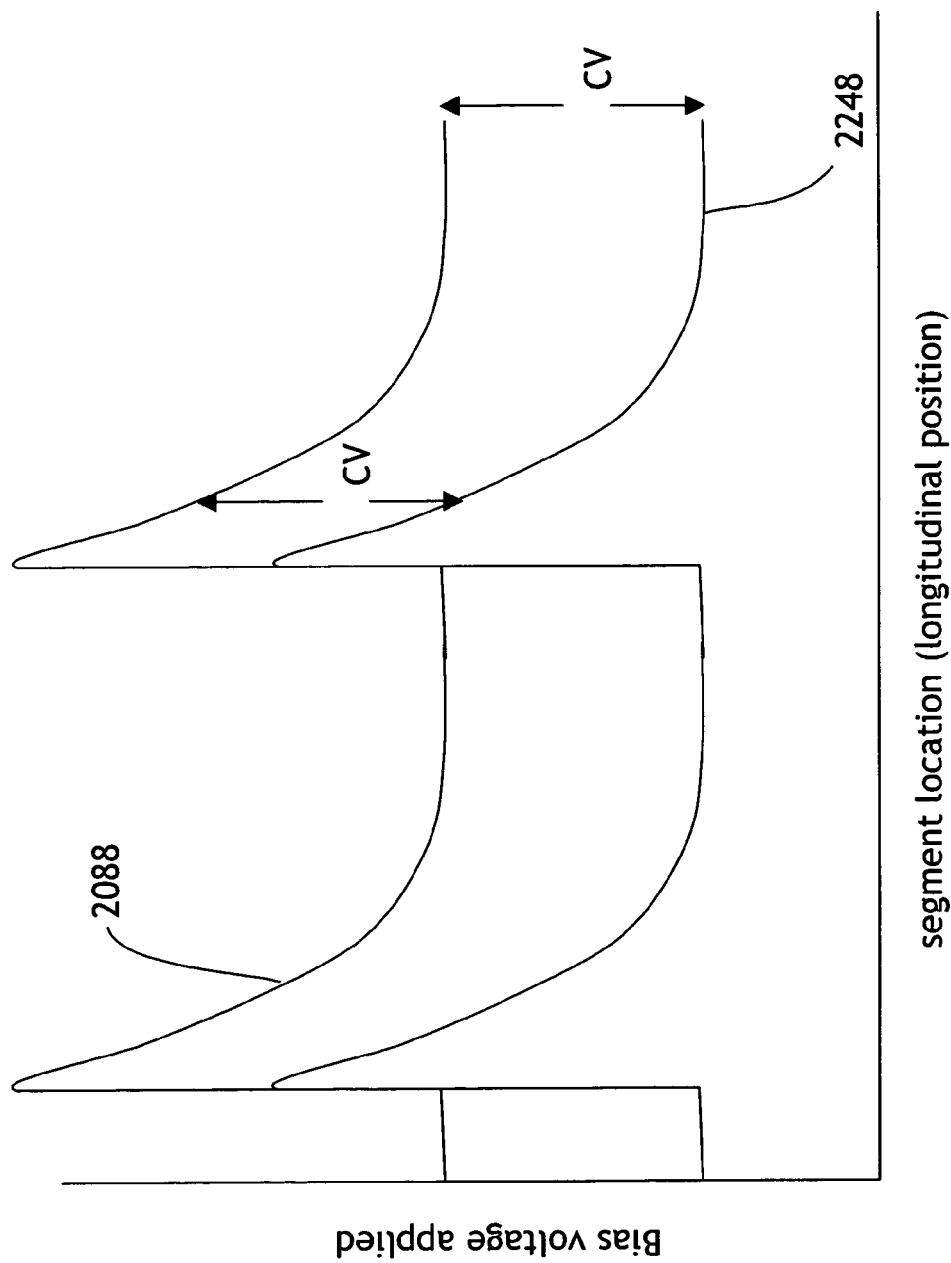
FIG. 4a is a graph of a selected pattern of the dc bias voltages applied to the segments of the inner and outer electrodes of a segmented FAIMS.

FIG. 4a illustrates schematically the dc bias voltages that are applied to the segments comprising the inner and outer electrodes of a segmented cylindrical FAIMS. Curve 2088 illustrates the dc bias voltages applied to the outer electrode 108 of FIG. 1, and curve 2248 illustrates the voltages applied to the inner electrode 124 of FIG. 1. The horizontal x-axis in FIG. 4a represents the longitudinal position of a segment and the vertical y-axis represents the voltage applied to the given segment. In FIG. 4a it is assumed that the FAIMS electrodes are divided into a plurality of segments, the number of which may exceed the number shown in the simplified version of FAIMS appearing in FIG. 1. For simplicity, the curves shown in FIG. 4a are drawn as smooth traces, but should be a series of small steps similar to FIGS. 2a and 2b, where the number of steps is equal to the number of discrete segments in the electrodes. Still referring to FIG.

4a, the curves 2088 and 2248 illustrate the dc bias voltages applied to the FAIMS electrodes at one point in time. These voltages may change in magnitude as a function of time, or the pattern of voltages shown in FIG. 4a may move or be translated along the length of the segments.

Figure 4B:
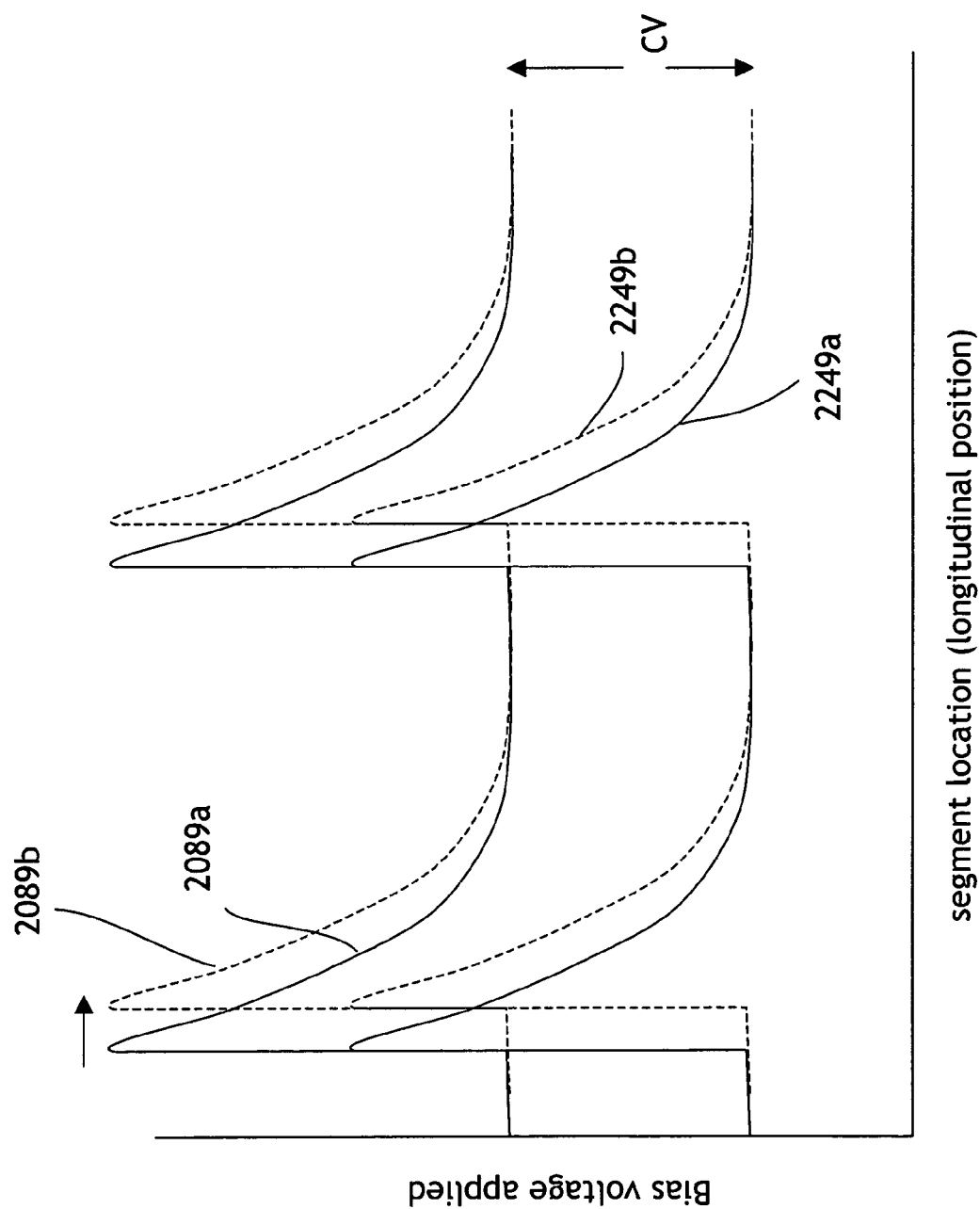
FIG. 4b is a graph of a selected pattern of the dc bias voltages applied to the segments of the inner and outer electrodes of a segmented FAIMS, at a first time and at a second later time.

Referring to FIG. 4b, the pattern of applied dc bias to the outer electrode at a first point in time is shown as trace 2089a whereas the trace 2089b illustrates the distribution of applied dc bias to the segments at a second point in time. Similarly, at a first time the distribution of dc bias to the segments of the inner electrode is shown by trace 2249a, and at a second time at 2249b. An optional method of making this happen is to change the dc bias voltages of each of the segments to equal the dc bias voltage of the segment to the immediate left of the segment. This occurs at fixed intervals of time. A computer system controls the voltages to the segments in such a way to create a waveform of the type shown in FIG. 4b that appears to travel along the length of the segments. In other words the peaks of voltages on the traces 2089a are translated along the segments, so that the peak appears to be at a segment further to the right on FIG. 4b at a later point in time, and yet further to the right at another later point in time. Another new peak begins to appear at the first segments as the other peaks shown in FIG. 4b are translated to the right. The series of peaks continuously translate along the length of the series of segments. In this figure, the absolute voltage difference between each segment of the inner electrode and each segment of the outer electrode, where these pairs are at the same corresponding longitudinal position, is always constant at the preselected CV voltage difference. At some later time a new CV voltage difference may be selected, and the pattern of peaks shown in FIG. 4b continues to be translated along the segments, but with a new vertical difference between the trace 2089a and 2249a.

Referring again to FIG. 4a, it is a benefit of this translating pattern of voltages shown by the moving traces 2088 and 2248, that the pattern of voltages produces a longitudinal electric field in the analyzer region of the FAIMS electrodes. This longitudinal field carries the ions along the FAIMS analyzer somewhat analogous to a moving conveyor belt, where the peaks in FIG. 4a are protrusions in the conveyor belt where the material being transported is in packets between adjacent protrusions in the belt. However, in the FAIMS electrodes the packets of material located between the peaks are clusters of ions, moreover the ions with high mobility are readily moved by the longitudinal field and remain near the lower longitudinal field strength, represented by the lower slopes of the traces in FIG. 4b, whereas the ions with low mobility require additional longitudinal field strength to reach the velocity of the transporting peaks, or wavefronts, shown in FIG. 4b, and are therefore predominantly collecting along the steeper slope sections of FIG. 4b. This is shown schematically in FIG. 4c.

Figure 4C:
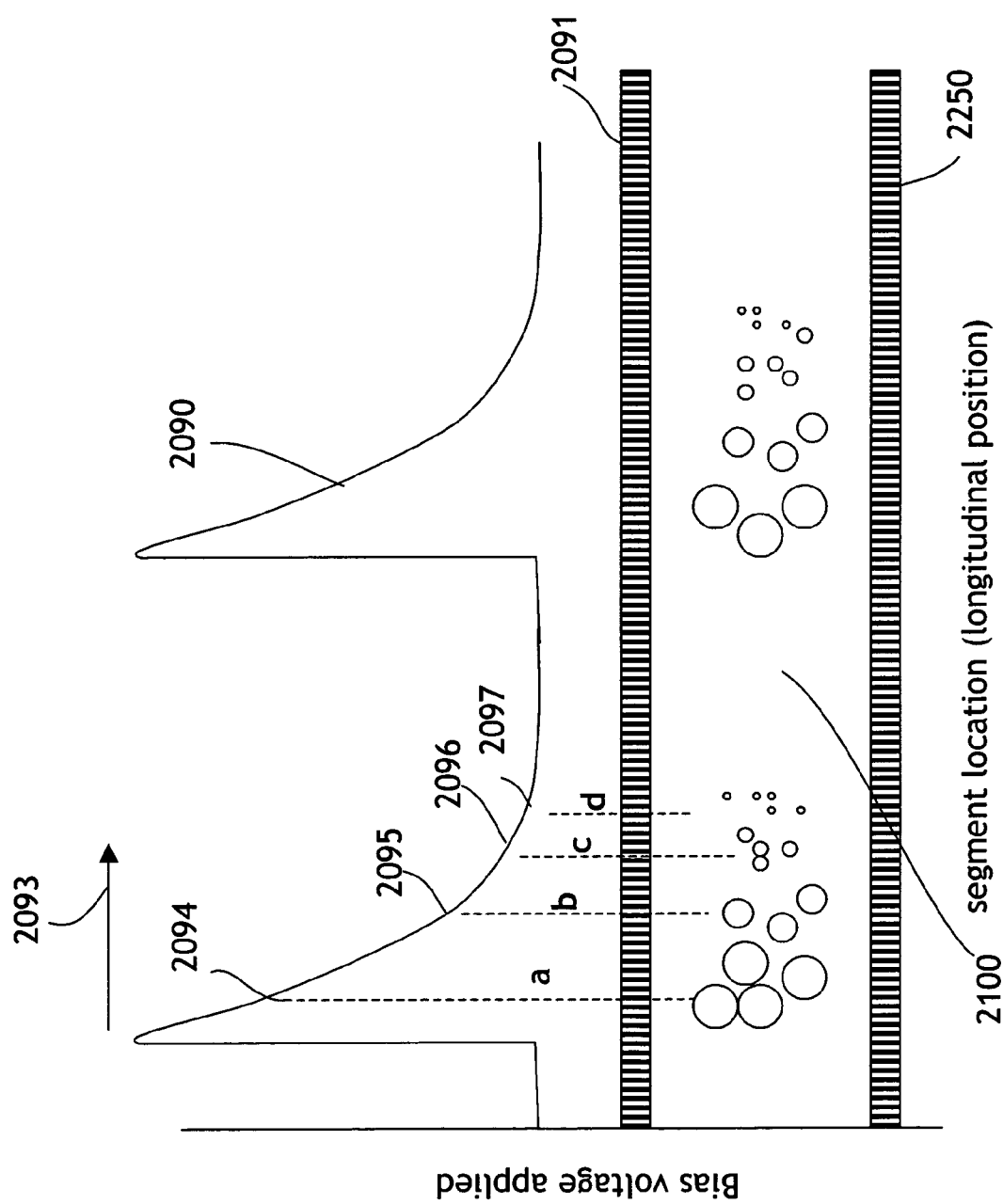
FIG. 4c illustrates a selected pattern of dc bias voltages applied to the outer segmented electrode, and the distribution of ions in the segmented FAIMS that results from a longitudinally traversed version of this pattern of applied dc bias voltages.

FIG. 4c shows a trace 2090 corresponding to the dc bias voltages applied to the segments of the outer electrode 108 of FIG. 1, assuming the number of segments significantly exceeds that shown in FIG. 1. The dc bias voltages applied to the segments of the inner electrode is not shown in FIG. 4c, but is offset from the trace 2090 by the difference equal to the CV. Similarly not shown is the applied asymmetric waveform voltage that is applied equally to all segments of the inner electrode, or optionally in some cases to the segments of the outer electrode, with polarity of CV and DV adjusted accordingly.

Still referring to FIG. 4c, the waveform is being translated from left to right as shown by the arrow 2093. The rate of translation, the voltage slope and magnitude and number of segments per peak shown in FIG. 4c are controlled by a not-shown computer system, or another suitable digital control device. The electronics and software to provide the dc bias voltage to each segment independently of the other segments, and to permit user selection of the properties of the waves in FIG. 4c are complex, but readily designed and fabricated.

The lower half of FIG. 4c is a schematic representation of the behavior of a series of ions that are being transported by the moving series of peaks in trace 2090 in the upper half of the figure. The ions are being transported through the analyzer region 2100 located between electrodes 2091 and 2092. Although it is preferable that these electrodes are cylindrical and segmented, these electrodes optionally are parallel and segmented. These electrodes optionally are fabricated using micromachining technology. For instance, the figures shown in this disclosure optionally are scaled in size down to sub-millimeter size. Nothing in this disclosure is intended to in any way limit the dimensions of the systems shown. The motion of the ions is controlled by conditions of E/N, which in turn depends on dimensions of the electrodes, spacing between electrodes, applied voltages, as well as conditions of gas pressure and temperature.

Still referring to FIG. 4c, the ions are transported through the analyzer region 2100 by the longitudinal fields generated by the dc bias voltages applied to the series of segments comprising the inner and outer segmented electrodes of a preferably cylindrical geometry FAIMS. Only a small portion of the segmented outer cylindrical electrode 2091 and of the segmented inner electrode 2250 are shown. The segments are represented by the vertical lines within the electrodes 2091 and 2250. Ions are pulled by the longitudinal fields in a direction from left to right in FIG. 4c, moreover since the wavefronts or peaks in trace 2090 are also being translated along the segments of 2091 and 2250, the ions move along the analyzer region in response to this moving longitudinal field. The longitudinal field is optionally non-uniform at the front of the peaks shown as trace 2090 in FIG. 4c. The slope of the voltage change per segment in the region shown as 2097 of trace 2090 is low, which illustrates that the voltage difference between adjacent segments is small and therefore produces a longitudinal electric field that is relatively weak. By way of comparison, the slope of the voltage change per segment in the region shown as 2094 of trace 2090 is high, which illustrates that the voltage difference between adjacent segments is high and therefore produces a longitudinal electric field that is relatively strong. The ions which have high mobility, and usually small cross sectional diameter, require only a weaker electric field to achieve the velocity 2093 of the moving wavefront, and therefore tend to be found at a location shown by dashed line "d" in FIG. 4c. The ions with larger cross section diameter, shown by larger circular ions in the analyzer region 2100, require stronger longitudinal fields to maintain velocity 2093, and therefore are traveling with the wavefront 2090 at approximately a region represented by the dashed line "a" in FIG. 4c. Other ions distribute according to their low-field mobility in regions shown by dashed lines "a", "b", "c", and "d". This arrangement-in-space longitudinally of ions in relation to their low-field mobility is expected to occur at every peak of the moving wavefront in trace 2090, and a second set of ions is therefore shown aligned similarly with the second peak in trace 2090.

Still referring to FIG. 4c, the position of a given ion relative to the peaks in trace 2090 is dependent on conditions including the slope of the trace 2090, the velocity 2093 that the wavefronts in trace 2090 proceeds down the length of the segmented FAIMS electrodes, as well as ambient conditions of gas composition, gas pressure and temperature.

Of course it is to be understood that those ions shown in FIG. 4c are pre-selected to be transmitted through FAIMS at the applied conditions of asymmetric waveform voltage and compensation voltage. In other words, the ions shown are a subset of the original mixture of ions, and this particular subset of the mixture is selected by the FAIMS on the basis of the high-field properties of the ions. The separation illustrated in FIG. 4c is therefore a combined FAIMS separation based on high-field mobility properties of the ions, and a second separation based upon the low field mobility of the ions. Other types of ions of the original mixture with high-field ion mobility properties not appropriate for transmission at the applied conditions of DV and CV have collided with the electrodes, and are not shown in FIG. 4c. The ions pre-selected by the conditions of DV and CV are transmitted in FAIMS, and are further distributed physically along the segmented electrodes by the moving wavefront 2090. By operating at a different combination of DV and CV, a different set of ions is isolated out of the original mixture on the basis of their high-field mobility properties, and this different subset of ions is also separated by their low field mobility properties as shown in FIG. 4c. This multi-dimensional separation may be performed over a wide range of CV, DV and moving wavefront conditions.

It is preferable that the separations based on FAIMS and the low-field mobility shown in FIG. 4c be carried out using cylindrical FAIMS. The cylindrical FAIMS focuses the selected subset of ions that are transmitted at the DV and CV, and therefore minimizes loss through collision with the electrodes. The stationary longitudinal electric fields generated in the voltage patterns applied to FAIMS segments as shown in FIGS. 2a and 2b, or the moving longitudinal electric field generated by moving patterns shown in FIGS. 4a to 4c, operate with highest ion transmission efficiency when the ions are focused between the electrodes by the focusing properties of cylindrical electrodes. Similar longitudinal fields can be generated in several versions of FAIMS, some non-limiting examples which include segmented parallel plate electrodes, stacks of three or more segmented parallel electrodes, and several cylindrical and spherical versions of electrodes, within the scope of the present invention. The FAIMS electrodes may be fabricated in many sizes and using many fabrication technologies, and remain within the scope of the present invention.

FIGS. 5a through 5e illustrate yet another embodiment of the present invention. The upper half of the figures illustrates the dc bias voltages applied to a series of segments of a cylindrical geometry FAIMS. The lower half of the figure illustrates a diagrammatic rendition of ions in the analyzer region 307 between an outer segmented-electrode 306 and an inner segmented-electrode 305.

Figure 5A:
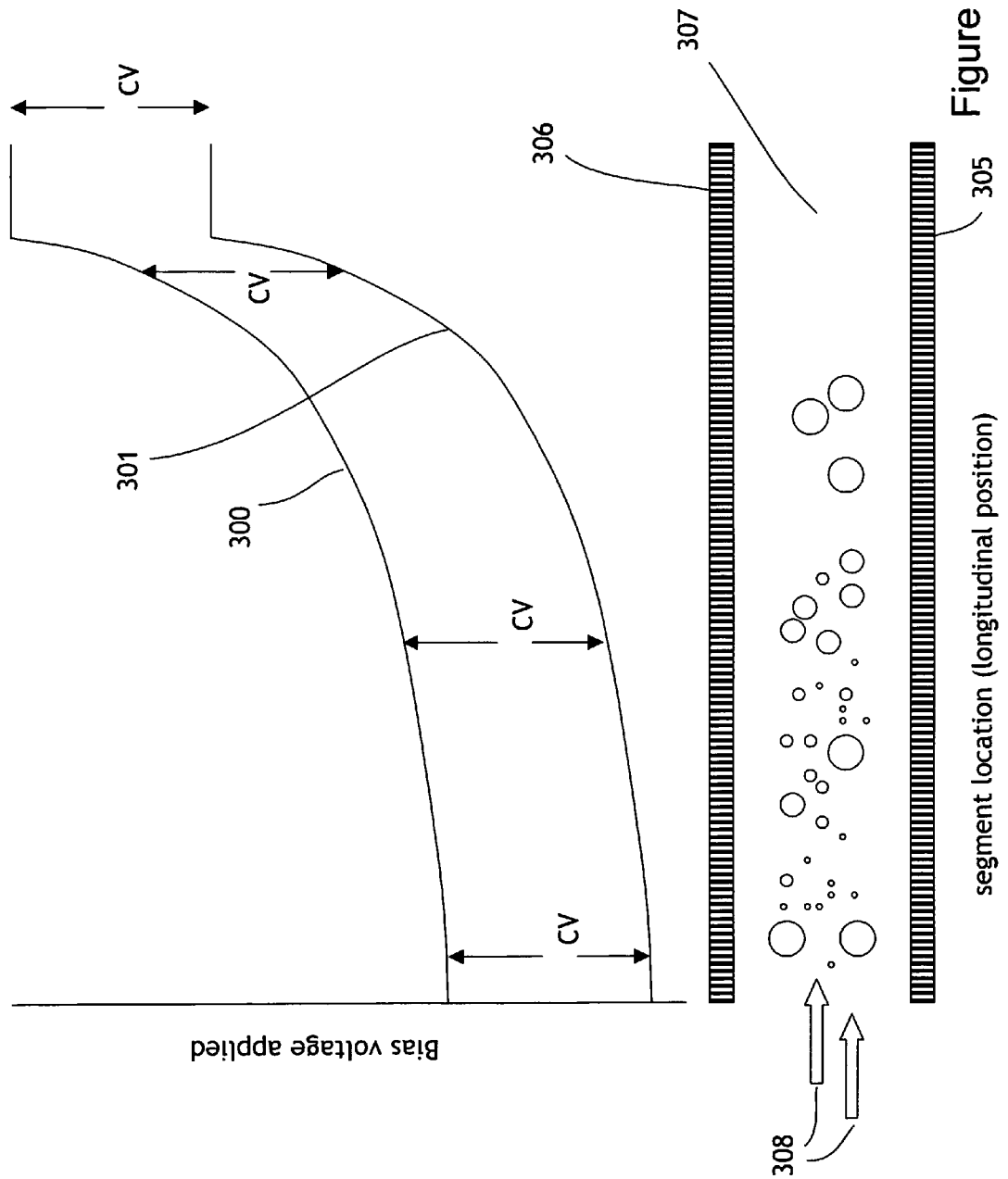
FIG. 5a illustrates the pattern of dc bias voltages applied to the outer segmented electrode and inner segmented electrode, and the distribution of ions in the segmented FAIMS prior to equilibration in response to this pattern of applied dc bias voltages.

FIG. 5a illustrates a mixture of ions being carried along the analyzer region 307 by a flow of carrier gas 308 indicated by wide arrows. A static electric field gradient in the longitudinal direction is formed as a result of the applied dc bias voltages, illustrated by curves 300 and 301, applied to the segments of the outer and inner segmented-electrodes, respectively. The lower half of the diagram shows a portion of the outer segmented-electrode 306 and an inner segmented-electrode 305. At a first period of time shown by FIG. 5a, the mixture of ions comprising a subset of the original mixture, this subset formed by the FAIMS separation, is being carried by a flow of gas in the analyzer region 307. Note that near the left edge of the figure, the mixture is heterogeneous, and comprised of ions of all sizes to represent ions of a range of low-field mobility values. The ions that are small in cross section have high values of low-field mobility and therefore reach equilibrium at weaker longitudinal field than do ions with wide cross section. This means that few ions of small size can travel far into the space between the electrodes, since the longitudinal field gets stronger as the voltage differences between adjacent segments increases.

Figure 5B:
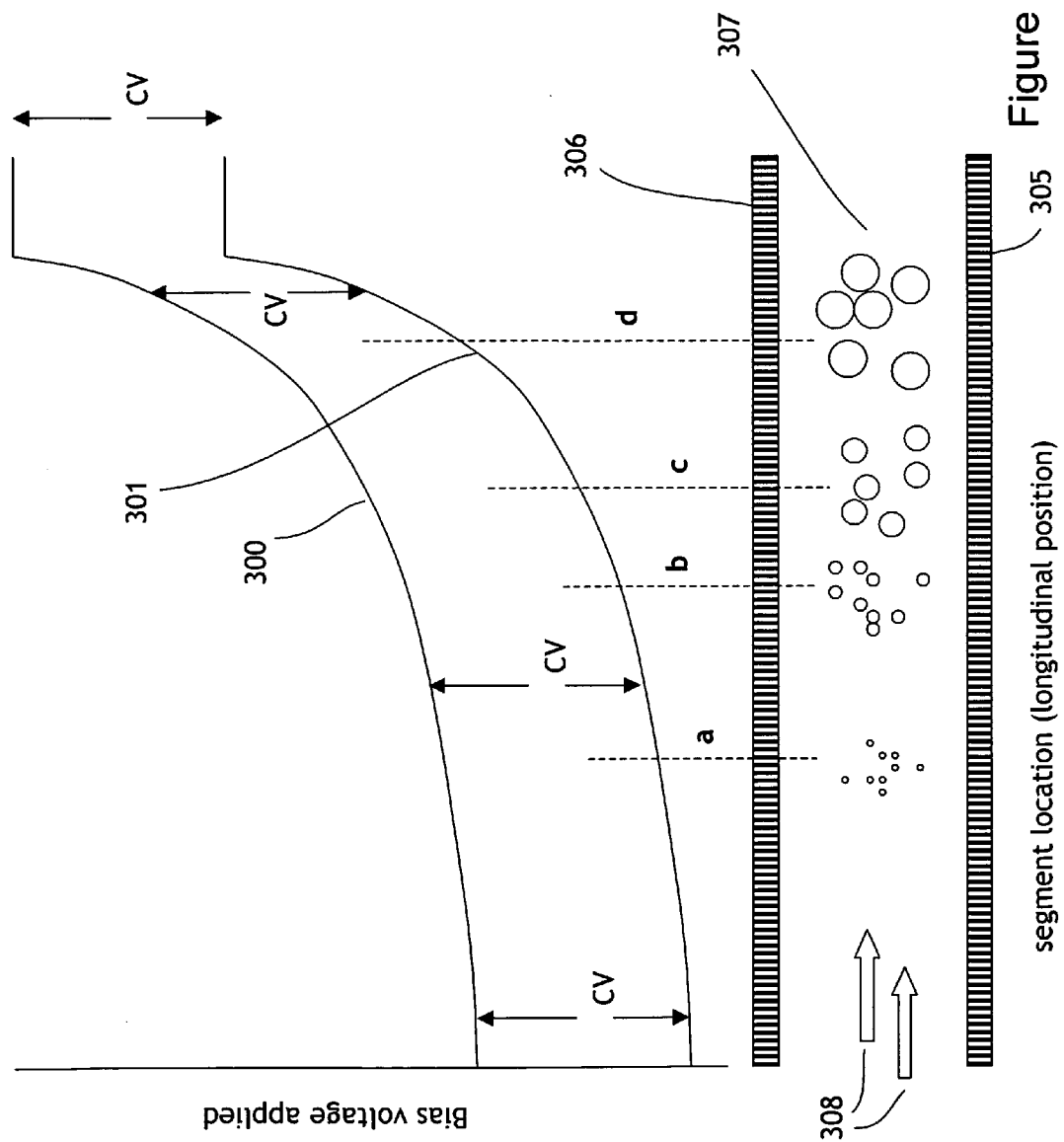
FIG. 5b illustrates the pattern of dc bias voltages applied to the outer segmented electrode and inner segmented electrode, and the distribution of ions in the segmented FAIMS at a time after equilibration of the ions in response to this pattern of applied dc bias voltages.

FIG. 5b illustrates the ion composition at a time that is later than in FIG. 5a. For simplicity in the diagram, no new ions are arriving. Optionally the ion stream is interrupted up-stream from the portion of the electrode represented by FIG. 5b. Since the cylindrical FAIMS device is focusing, and the ions prevented from colliding with the electrode walls, the ions can be collected as shown in FIG. 5b for some period of time until the ion cloud is sufficiently dense that diffusion and ion-ion mutual repulsion degrade the effectiveness of ion collection. In FIG. 5b the ions that were pre-selected on the basis of their FAIMS properties, namely high-field behavior, are now additionally separated in space along the electrodes on the basis of their low-field mobility. If the potentials shown by traces 300 and 301 are replaced by dc biases equal on all segments, with CV remaining as a difference in voltage between an outer segment and inner segment at a same longitudinal location, then the ions distributed as shown in FIG. 5b are carried out of the analyzer region and to a detector, and convert the longitudinal distribution along the electrodes into a time-of-arrival distribution that represents the spectrum of the low field mobility of the ions that are in the subset selected by conditions of CV, DV and other ambient conditions. This time-dependent ion arrival distribution can readily be further separated or detected using an electrometer or mass spectrometer as some non-limiting examples.

Figure 5C:
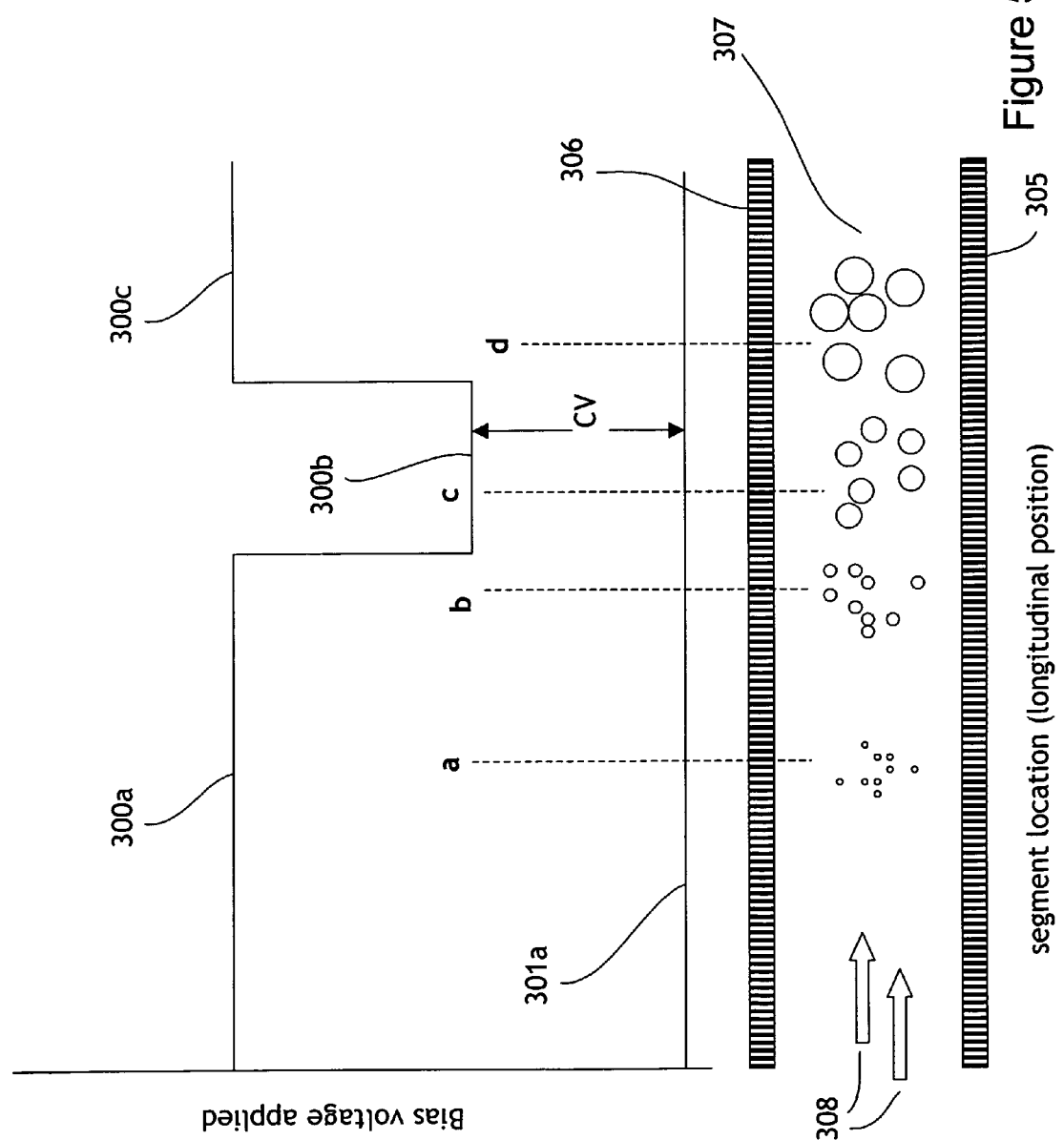
FIG. 5c illustrates a new pattern of dc bias voltages applied to the outer segmented electrode and inner segmented electrode, and the distribution of ions in the segmented FAIMS prior to equilibration of the ions in response to this new pattern of applied dc bias voltages.
Figure 5D:
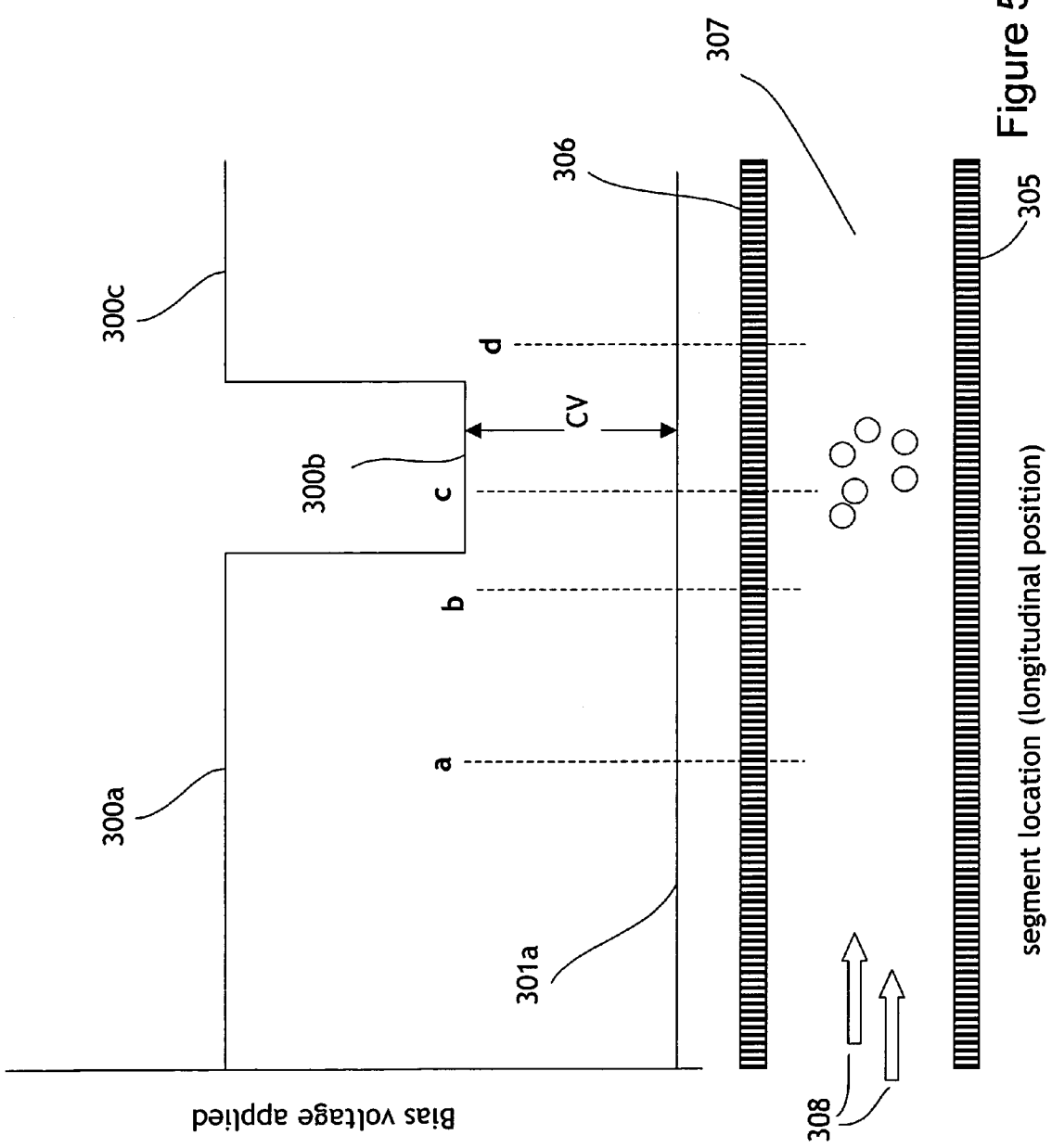
FIG. 5d illustrates a new pattern of dc bias voltages applied to the outer segmented electrode and inner segmented electrode, and the distribution of a new subset of ions in the segmented FAIMS after removal of some of the ions by application of this new pattern of applied dc bias voltages.

Alternatively, as shown in FIG. 5c, a portion of the ions are selectively retained in the analyzer for further analysis, while other ions are selectively discharged by collision with the electrode walls. In FIG. 5c the voltages applied to the series of segments of the outer segmented-electrode is represented by curves 300a, 300b and 300c. Similarly the voltage applied to the segments of the inner segmented-electrode is represented by curve 301a. Unlike the voltages shown in FIGS. 5a and 5b, portions of the segmented electrodes no longer have the voltage difference of CV between the outer and inner segments of the electrodes. In a previously unknown step, at least a portion of the same electrode system is operated at a CV that does not transmit. In the example shown in FIG. 5c, the segments of the part of the segmented electrodes corresponding to 300a and 300c are not separated by a voltage equal to CV. Within a second, separate region along the segmented electrodes, shown as part 300b the voltage difference is equal to CV. Only ions that occupy the longitudinal region corresponding to the part of the trace indicated by 300b are in a stable balance between the effects of DV and CV. Elsewhere, including region 300a and 300c, the ions collide with the electrodes.

Referring again to FIG. 5b, the ions of differing ion cross section have accumulated in regions a, b, c and d along the length of the segmented electrodes. If the voltages applied to the segmented electrodes are rapidly changed to those shown in FIG. 5c, it is clear that the ions in regions indicated as a, b and d are no longer in conditions suitable for transmission, whereas ions located near the dashed line marked by c are still transmitted. This is shown schematically in FIG. 5d, in which only those ions in the region indicated as c remain in the analyzer region. The ions formerly occupying the regions indicated as a, b and d have collided with one of the electrode surfaces and been neutralized.

Figure 5E:
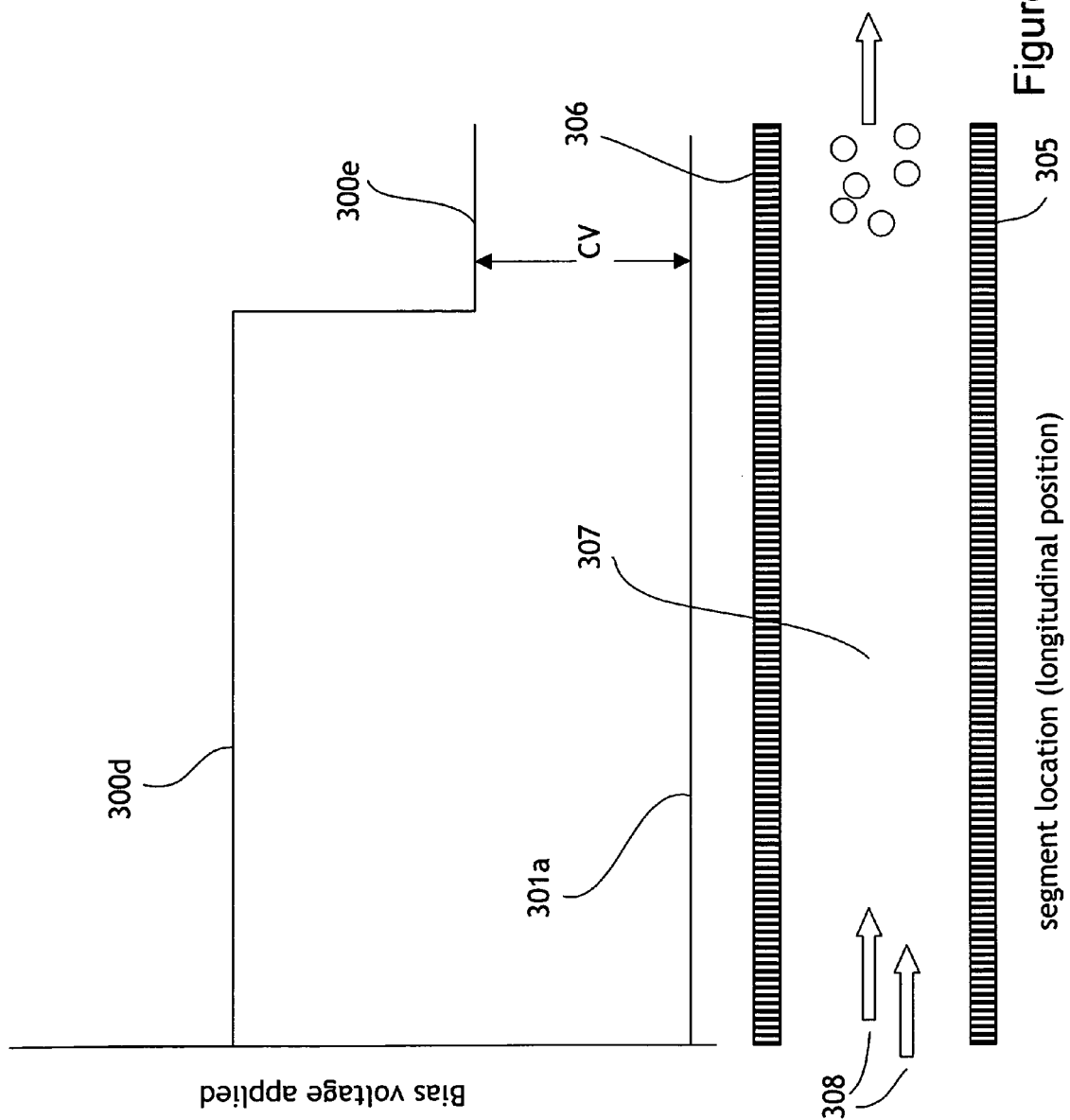
FIG. 5e illustrates a new pattern of dc bias voltages applied to the outer segmented electrode and inner segmented electrode, and the distribution of ions in the segmented FAIMS while the subset of selected ions is being transported by a flow of gas.

Of course, since the ions are being carried by a flow of gas, the region 300b must then travel with the ions to maintain transmission as they are carried by the carrier gas flow. FIG. 5e illustrates the ions after having traveled with the gas, and shows that the electrode segments at locations adjacent to the ions, namely in section 300e of the upper trace, continue to operate with a difference between the inner and outer electrodes equal to CV. Elsewhere, the ions collide with the electrode walls.

An unforeseen benefit of segmentation of the electrodes is the opportunity to operate selected regions of the segmented electrodes at other than the CV suitable for transmission of the original subset of ions. In this case, the original subset of ions is separated from a correspondingly more complex mixture at a particular combination of CV, DV and other ambient conditions. Once so separated, changes of voltage applied to portions of the segmented electrodes so as to be other than the original CV and DV combination result in loss of selected groups of ions of the original subset of ions, resulting in high selectivity to very few compounds out of a very complex mixture.

The new method to achieve high resolution is illustrated in FIG. 5c. The original subset of ions, composed of four ions of comparable high-field mobility behavior and thus all transmitted in FAIMS at the original CV, DV conditions but having differing low-field mobility, was further separated to yield a single type of ion, shown being selectively transmitted out of FAIMS in FIG. 5d and FIG. 5e. In this case, the detector does not require a time-dependent measurement. Only ions that had both (a) high-field mobility behavior to be passed through FAIMS at the original CV and DV, and (b) had a selected low-field mobility were transmitted through FAIMS to be detected or further analyzed. It is beneficial that this second time-dependent analysis be eliminated, for simplification of the detection, for example so that the detector measures only the one component of interest, perhaps being an explosive compound in the case of a highly selective application related to homeland security. It is also beneficial that only one of the ions be transmitted out of this system when the detection system is not suitable for time sensitive measurement, for example when using a quadrupole mass spectrometer.

Similarly, the moving voltage patterns illustrated with reference to FIGS. 4a-4c can also be operated to provide only one of the low-field mobility separated ions to the detector or to another analyzer for further analysis. It is a benefit of the segmented electrode system, that ions can be rejected from the device by changing the voltages of certain segments so that the voltage difference between a segment of the outer electrode and the segment in the inner electrode in a specific longitudinal region is no longer CV.

Figure 6A:
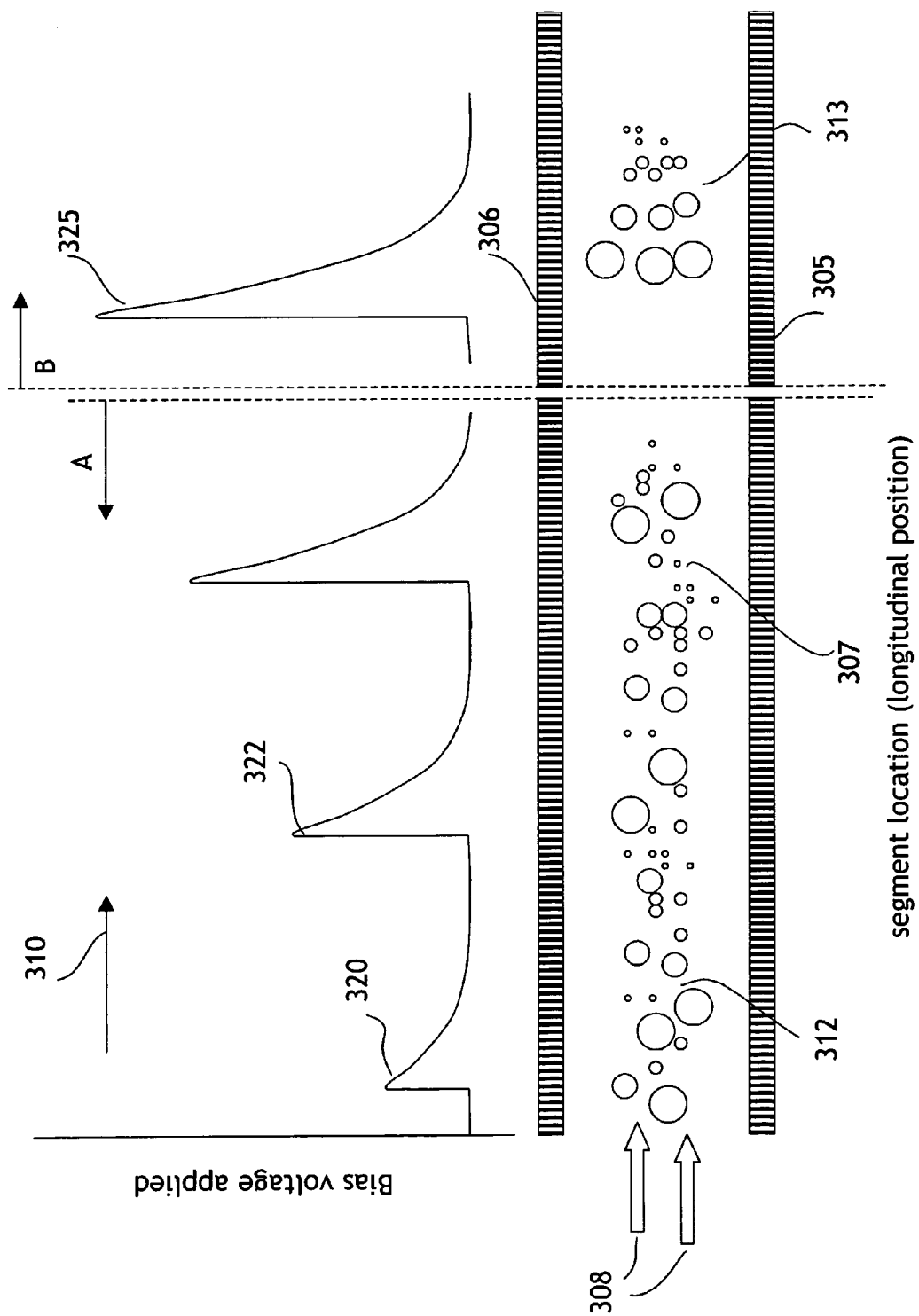
FIG. 6a illustrates a pattern of traveling dc bias voltages applied to the segmented outer electrode of FAIMS, and the distribution of ions between the inner and outer electrodes in response to this applied pattern.

FIG. 6a illustrates a region of a segmented cylindrical FAIMS, the electrodes and diagramatic rendition of ions in the analyzer appearing in the lower half of the figure and the voltages applied to the outer segments shown as the trace in the upper half of the figure. The dc bias applied to the other electrode set is identical but offset in voltage by the selected value of CV. The dc bias voltages applied to the segments is controlled by a computer so that the peaks 320, 322 and others are being translated at velocity 310 along the series of segments from left to right in this figure.

Still referring to FIG. 6a, dashed vertical lines divide the figure into a left portion indicated by arrow A, and a right portion B. A part of the segmented electrodes between these two dashed lines has been omitted for clarity in this figure. An analyzer region 307 is located in the annular space between the outer segmented-electrode 306 and the inner segmented-electrode 305. Only a portion of the annular region is shown in FIG. 6a.

Ions from a not-shown ion source are delivered to the analyzer region and the complex sample mixture of ions is separated on the basis of the high-field mobility properties of the ions prior to their arrival at the left-hand edge of FIG. 6a. All of the types of ions shown flowing in the analyzer region 312 in FIG. 6a comprise a subset of the more complex sample mixture of ions, indicating that at a given value of CV and DV, in many cases separation is not complete, and a simplified subset of the mixture is transmitted through FAIMS. This has previously been discussed with regard to mixtures including tryptic digests of proteins ionized using electrospray ionization.

Still referring to FIG. 6a, the complex sample mixture of ions is subjected to the passage of the longitudinal electric field gradients formed by the voltages applied to consecutive segments of the segmented inner electrode 305 and the segmented electrode 306. At the left edge of FIG. 6a, the peaks have low voltage, as shown as peak 320, but the peaks increase in voltage as they migrate along the segmented electrodes. This has the beneficial effect of capturing the ions gradually to minimize collisions with the electrodes. At some distance further along the electrodes, such as the portion beyond the dashed line B, all of the peaks 325 applied to the segments have the same voltage, and are migrating along the electrodes at a selected velocity 310. It is optionally possible that the peaks continue to increase in voltage, and also possible that the longitudinal distances between the peaks be increasing or decreasing as they migrate along the electrodes. These properties of the voltages applied to the series of consecutive segments is under computer control, and many optional patterns and voltages are readily feasible.

Still referring to FIG. 6a, the ions gradually arrange themselves in an order of low-field mobility, according to the slope of the electric field gradient produced by application of the voltages such as the peak 325. In region 313, at some distance along the segmented electrodes, the ions are arranged in longitudinal direction in dependence upon their low-field mobility. If the ions are transmitted in this manner to the detector, or to a further analyzer after passage through this device, the longitudinal in-space distribution becomes a time-of-arrival pattern also in dependence of the low-field mobility of the ions. Recall that these ions have been pre-selected on the basis of their high-field mobility prior to the separation on the basis of low-field mobility that is shown in FIG. 6a.

Still referring to FIG. 6a, the detection system to which the ions are delivered after passing out of the FAIMS electrodes must be suitable for the time-of-arrival pattern of the ions. An electrometer detector or a time-of-flight mass spectrometer are non-limiting examples of suitable detectors. For good separation resolution of the ions it is necessary that the in-space distribution of the ions shown in region 313 of FIG. 6a, be retained during the transport of the ions out of the electrodes. In this regard the FAIMS system shown in FIG. 1 would not necessarily be suitable, because the resolution of the ions distributed in-space may be lost during transport of the ions from the end of the segmented parts of the inner electrode 224 and outer electrode 208, to the ion outlet 230. The ion outlet in the FAIMS system shown in FIG. 1 is on one side of the outer electrode 208, and the ions from everywhere in the annular analyzer region 228 are carried by a gas flow converging to the ion outlet 230, with concomitant loss of spatial resolution.

Figure 7:
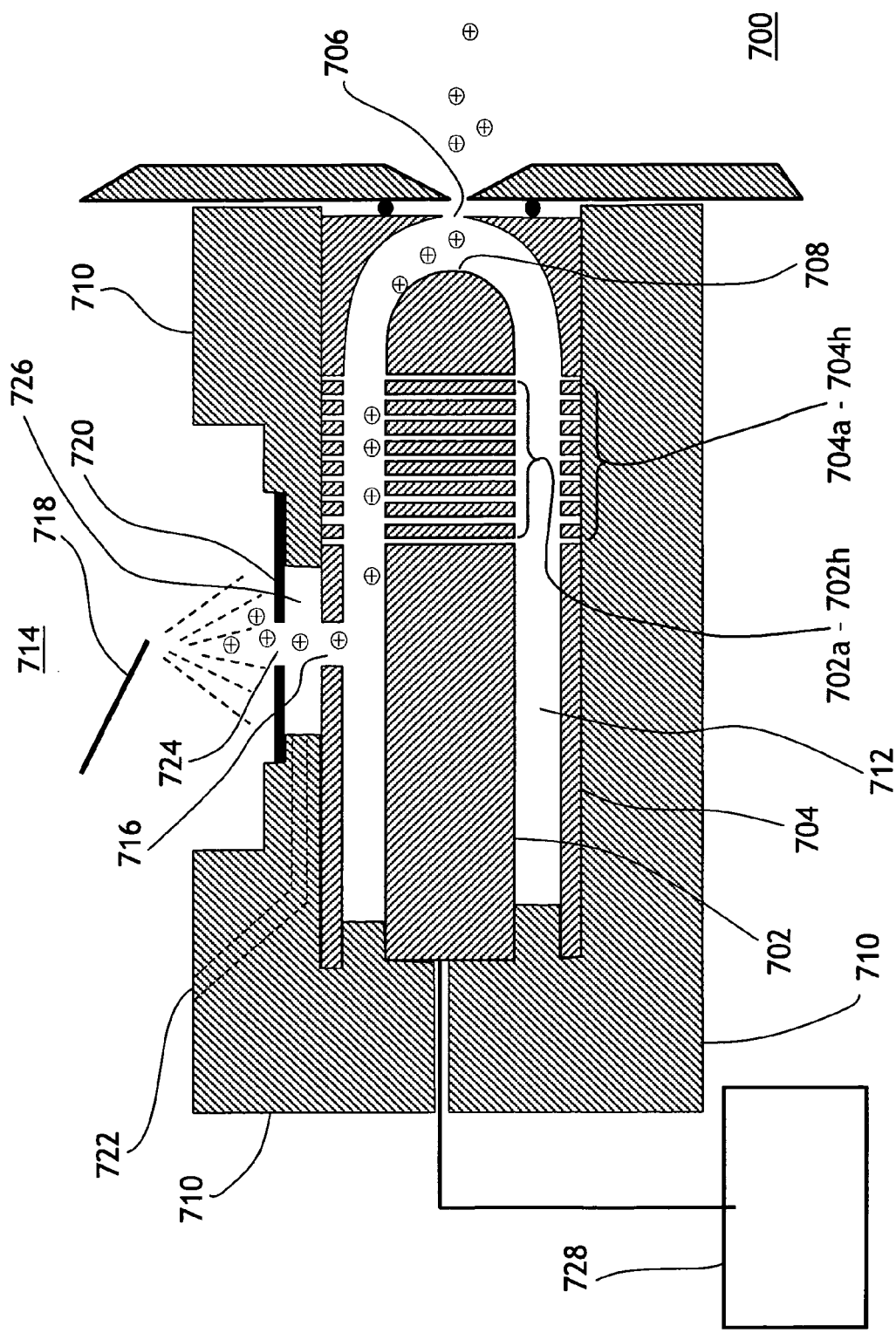
FIG. 7 is a simplified cross-sectional view of a cylindrical geometry FAIMS according to an embodiment of the instant invention, including a segmented inner electrode having a curved surface terminus.

Referring now to FIG. 7, shown is a longitudinal cross-sectional view of a FAIMS system 700 including a segmented inner electrode 702 having segments 702a-702h, and a segmented outer electrode 704 having segments 704a-704h, and having an ion outlet orifice 706 disposed adjacent to a hemispherical tip 708 of the inner electrode 702. According to FIG. 7, the inner electrode 702 and the outer electrode 704 are supported in a spaced-apart arrangement by an insulating material 710 with high dielectric strength to prevent electrical discharge. Some non-limiting examples of suitable materials for use as the insulating material 710 include Teflon®, and PEEK. Furthermore, the segments 702a-702h and 704a-704h of the inner and outer electrodes, respectively, are supported and separated one from the other by a similar insulating material, such as for instance Teflon® or PEEK. The insulating material between the individual segments of an electrode is necessary not only to physically support the segments in space, but also to allow application of different voltages between segment pairs of the inner and outer electrodes. Preferably, the insulating material forms a gas-tight seal between adjacent segments of a same electrode. Optionally, the insulating material between the segments is recessed below the electrode surface facing analyzer region 712.

An electrospray ion source 714 is disposed in fluid communication with an ion inlet 716 of the FAIMS system 700. Ions are formed near the tip of an electrospray needle 718 and drift towards a curtain plate 720. The curtain gas, introduced below the curtain plate 720 via a passageway 722, divides into two flows, one of which exits through an aperture 724 in the curtain plate 720, to prevent neutrals and droplets from entering the curtain plate aperture 724. Ions are driven against this gas by a voltage gradient between the needle 718 and the curtain plate 720. A field generated in the desolvation region 726 between the curtain plate 720 and the FAIMS outer electrode 704 pushes ions that pass through the aperture 724 in the curtain plate 720 towards the ion inlet 716 of the FAIMS system 700. A portion of the curtain gas flows into the ion inlet 716 and carries the ions along the length of the FAIMS electrodes through analyzer region 712 to the ion outlet orifice 706.

A high voltage asymmetric waveform is generated by supply 728 and is applied to the inner electrode 702 of the FAIMS system 700, to produce an electric field that causes ions within the annular analyzer region 712 between the inner electrode 702 and the outer electrode 704 to oscillate between the inner electrode 702 and the outer electrode 704. The waveform is generated in such a way to cause the ions to move in a first direction in a strong field for a short time, followed by motion in the other direction in a weaker field for a longer time. Absent any change in ion mobility between the high field and low field portions of this applied asymmetric waveform, after each cycle of the waveform the ion returns to its original position relative to the surface of the electrodes. In practice, the mobility of many ions is different in strong and weak electric fields and for these ions the position after one cycle of the waveform is not identical to the starting position of the ion relative to the electrode surfaces. A second, direct current voltage, which is referred to as the compensation voltage (CV), is applied to eliminate or compensate for this change of position. If the compensation voltage is of a magnitude that eliminates or compensates for the change of position that would occur absent the compensation voltage, then the ion returns to the same relative location after each cycle of the waveform. Thus the ion does not migrate towards one or the other of the electrodes, and may therefore be transmitted through the FAIMS system 700. Other ions for which the compensation voltage is too high or too low to compensate for the net displacement of the ion relative to the electrodes during one cycle of the waveform, drift towards an electrode and are neutralized.

Still referring to FIG. 7, the segmentation of the inner electrode 702, and outer electrode 704 along a portion of the analyzer region 712 between the ion inlet 716 and the rounded terminus 708 of the inner electrode 702 provides a better solution compared to the system shown in FIG. 1, when retention of the ion spatial resolution in the longitudinal direction is required. In the so-called "domed version of FAIMS" shown in FIG. 7, the ions from the annular analyzer region 712 between the inner electrode 702 and the outer electrode 704 at a given longitudinal location along the inner electrode 702 are expected to converge uniformly toward the ion outlet 706 and arrive at the same time at ion outlet 706, largely independent of their original starting location around the circumference of the inner electrode 702.

Referring again to FIG. 6a, it is also an option to selectively remove some of the types of ions that are arranged spatially in region 313 prior to further analysis or detection external to the FAIMS system. In other words, if ions other than some selected type of ions are caused to collide with the electrodes, only the ion of interest is transmitted. This beneficially eliminates the need for the retention of spatial resolution.

Figure 6B:
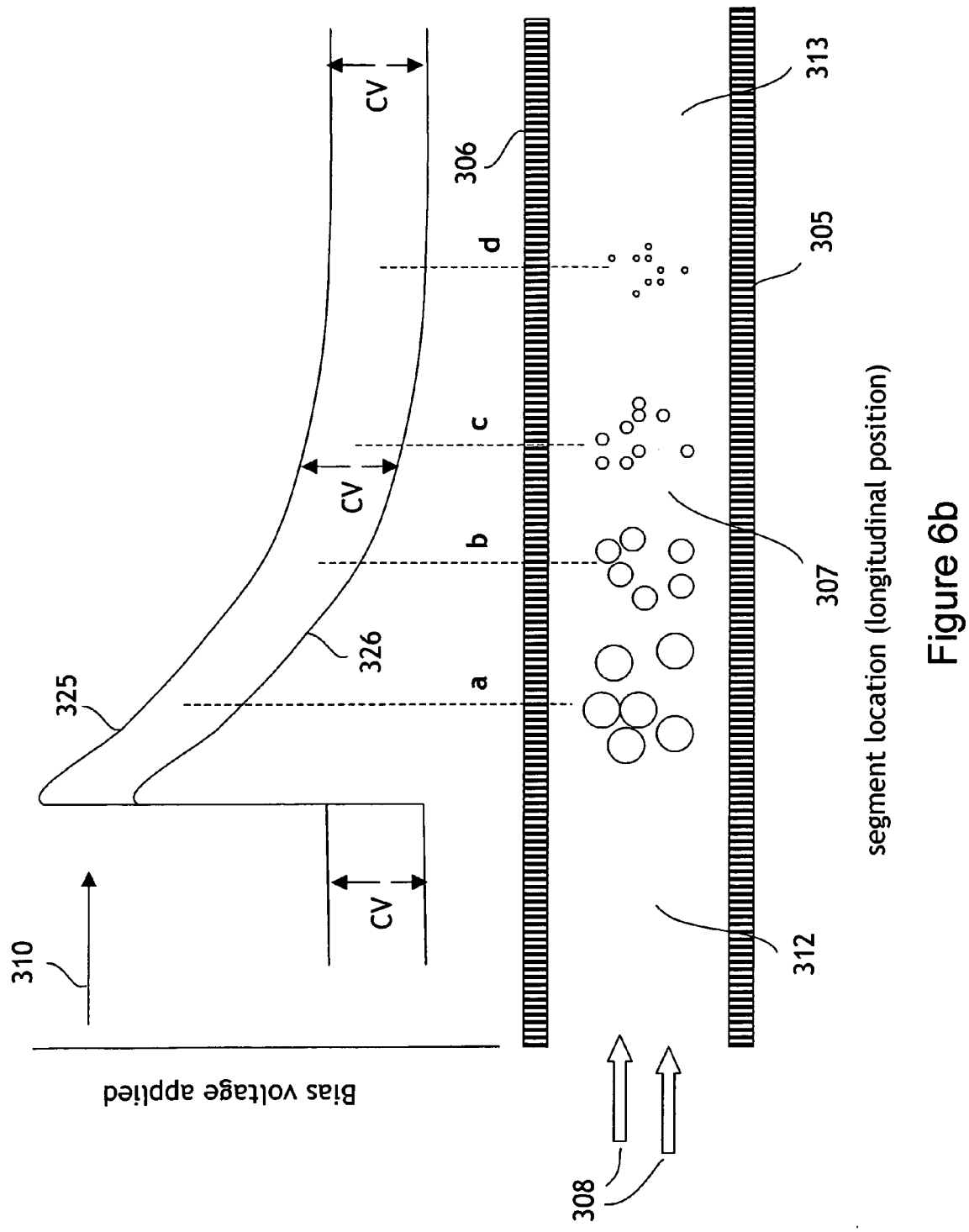
FIG. 6b illustrates a portion of the pattern of traveling dc bias voltages applied to the segmented outer electrode of FAIMS, and the equilibrium distribution of ions in response to this applied pattern.

FIG. 6b illustrates an expanded version of the segmented electrodes in the region of peak in trace 325, previously shown in FIG. 6a. The ions are arranged in space according to their low-field mobility, and four types of ions are illustrated with average longitudinal locations shown by dashed lines a, b, c and d. The trace 325 illustrates the voltages applied to the outer segmented-electrode 306, and the trace 326 illustrates the dc bias voltages applied to the inner segmented-electrode 305. The ions in analyzer region 307 are arranged according to their low-field mobility; moreover, this pattern is translated along the segmented electrodes at velocity shown by the arrow 310. The flow of carrier gas shown by arrows 308 in analyzer region 307 may be in the same direction as arrow 310, or optionally in the opposite direction. If the velocity shown by arrow 310 is much faster than the flow of gas, the positions of the ions relative to the trace 325 is largely independent of the flow of carrier gas. If the velocity of arrow 310 is comparable to the flow of carrier gas shown by arrows 308, the pattern of ions is at different locations relative to the trace 325 in dependence of the direction and velocity of the flow of carrier gas. In this non-limiting example, taken to facilitate the illustrated principles of ion transport in segmented FAIMS systems, the flow of carrier gas is assumed to be in the same direction as arrow 310, and at lower velocity than the velocity of the wavefront illustrated by trace 325.

Figure 6C:
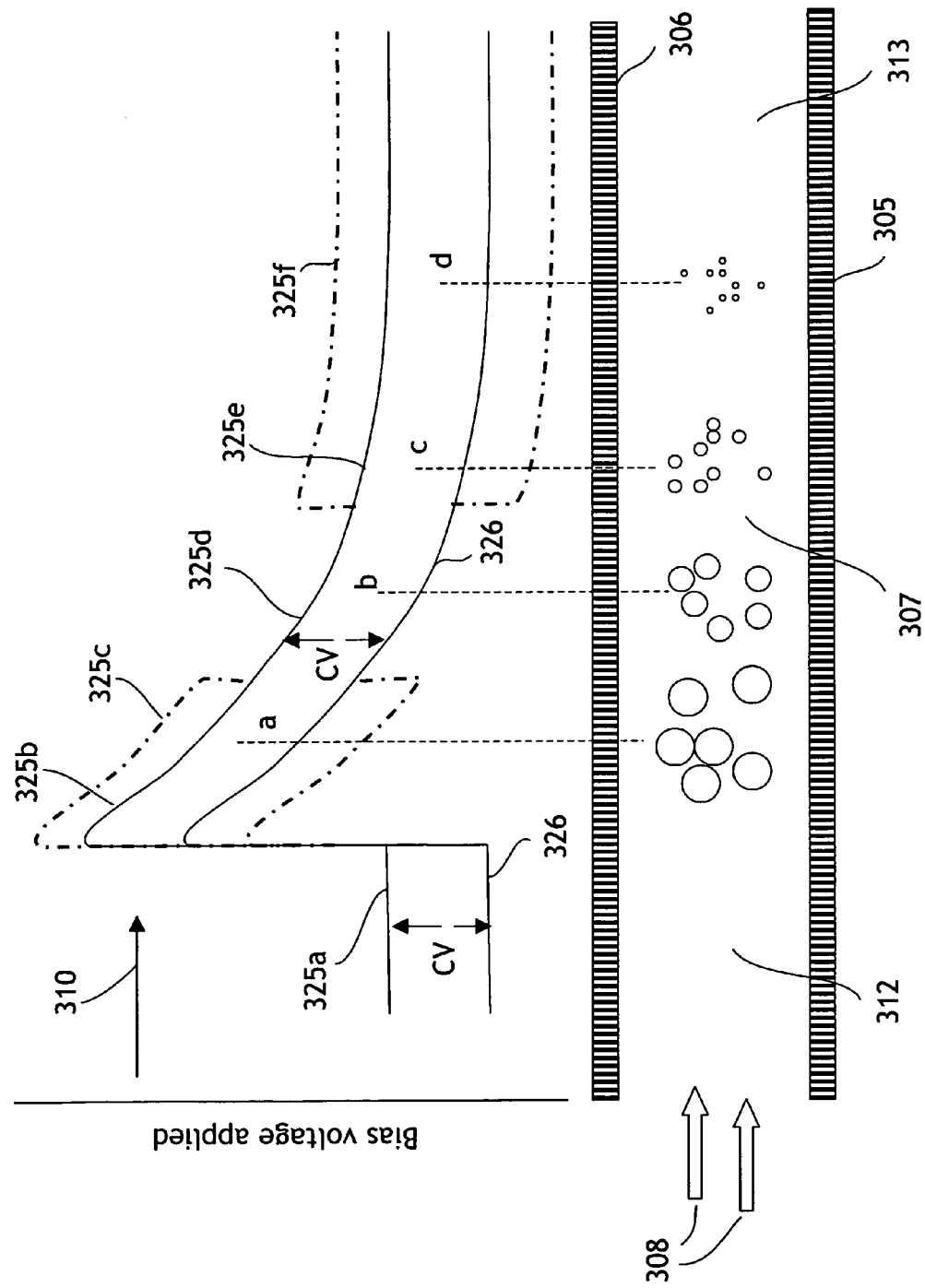
FIG. 6c illustrates several changes of voltages within a portion of the pattern of traveling dc bias voltages applied to the segmented outer electrode of FAIMS, and the equilibrium distribution of ions prior to their response to this modified applied pattern.

Still referring to FIG. 6b, all of the ions shown arranged into longitudinal positions indicated by the dashed lines a, b, c and d, may optionally be transported along the segments of FAIMS and delivered out of the ion outlet to another separation system, or to an ion detector. However, it is also possible to remove ions other than one type of ion from the analyzer region 307, so that only one type of ions with user-selected low-field mobility is transmitted to the ion outlet of FAIMS. FIG. 6c illustrates the voltage changes that are applied to the segmented FAIMS in order to reject the ions of the type accumulated at dashed line a, c and d, with retention of the ions of the type accumulated at dashed line b. The part of segmented FAIMS shown in FIG. 6c is the same as that shown in FIG. 6b.

Figure 6D:
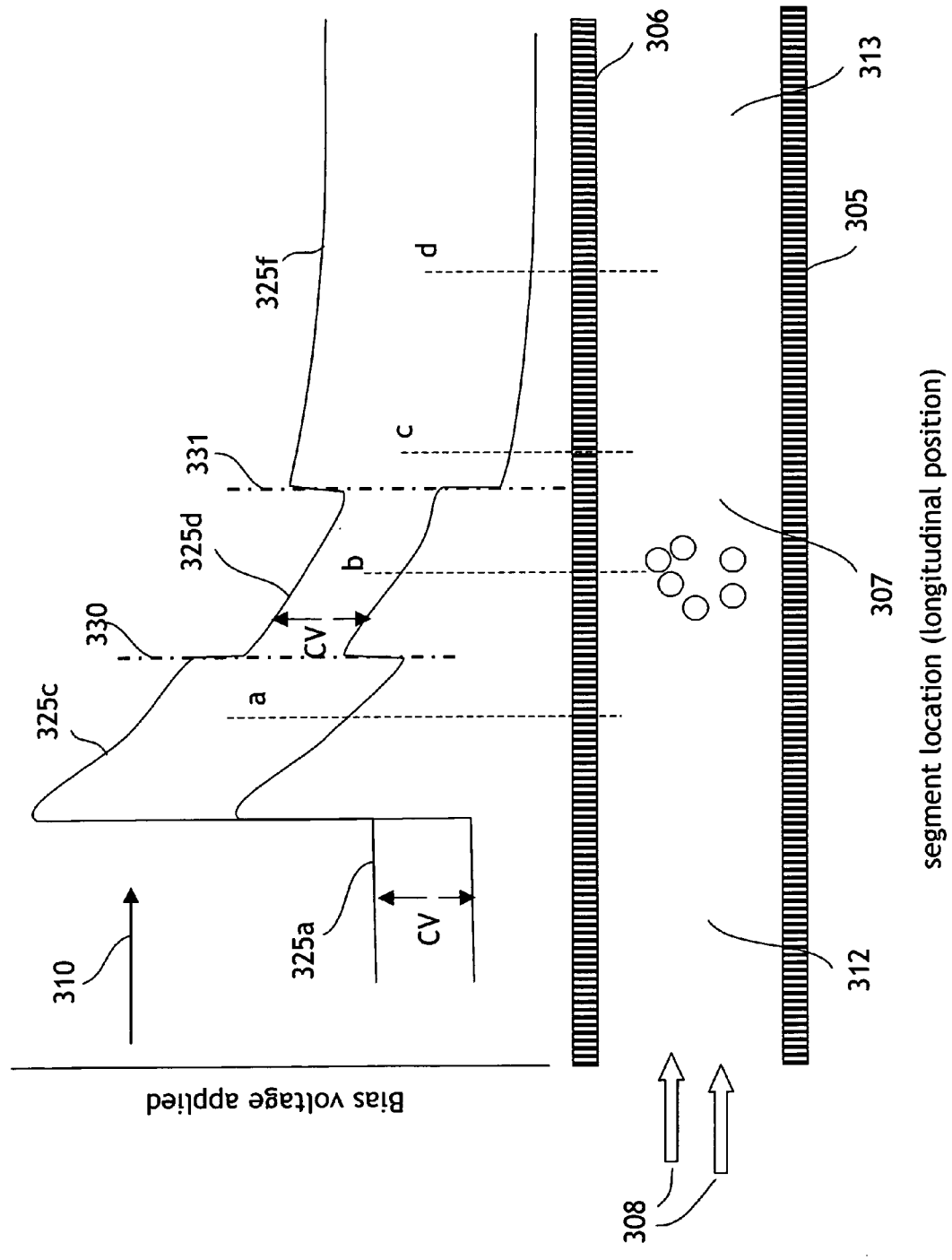
FIG. 6d illustrates the new pattern of voltages within a portion of the pattern of traveling dc bias voltages applied to the segmented outer electrode of FAIMS, and the new equilibrium distribution of ions prior to their response to this modified applied pattern.

Referring still to FIG. 6c, the upper solid trace composed of sections 325a, 325b, 325d and 325e is identical to trace 325 of FIG. 6b. At a selected location along the segments, the curve is changed by altering the voltages of the segments that were identified by 325b to new voltages shown by a dot-dash line 325c. Similarly the voltage along segment 325e is changed to voltages shown by dot-dash line 325f. The voltages in the region of dashed line b represent the ions that are selected to remain within the analyzer and the voltages in this particular range of segment 325d are identical to the voltages previously applied, including trace 325 of FIG. 6b. Analogous adjustments are made to trace 326, except that, as a non-limiting example, the voltage changes are made in the opposite direction and of equal magnitude. This change has important consequences to the ions arranged in the regions shown by dashed lines a, c and d, because differences in the dc bias voltage applied to the segments of the outer electrode and the dc bias voltage applied to the segments of the inner electrode no longer exactly equals the compensation voltage CV. In the area of the dashed line b representing the average location of the ions that are retained within the analyzer 307, the difference in the dc bias voltage applied to the segments of the outer electrode and the dc bias voltage applied to the segments of the inner electrode exactly equals the compensation voltage CV and the ions continue to be transmitted in FAIMS. The ions that are in regions where the newly applied CV differs from the original CV collide with the electrodes and are lost. FIG. 6d illustrates the ions between the outer segmented-electrode 306 and the inner segmented-electrode at a later time, after further translation along the segmented electrodes, and only one type of ion remains.

Still referring to FIG. 6d the ions that were located in the region of the dashed line b continue to be translated along the segmented electrodes by the moving wavefront illustrated by the curve 325a to 325f, because the slope of the longitudinal voltage gradient, giving rise to the longitudinal field within the analyzer region 307 is unchanged from that shown in FIGS. 6b and 6c, and the dc bias voltage difference between those segments of the outer segmented-electrode 306 and the inner segmented-electrode 305 remains equal to CV. The ions shown are selected on the basis of the FAIMS separation based on the high-field mobility properties of the ions, as well as upon their low-field mobility.

Figure 6E:
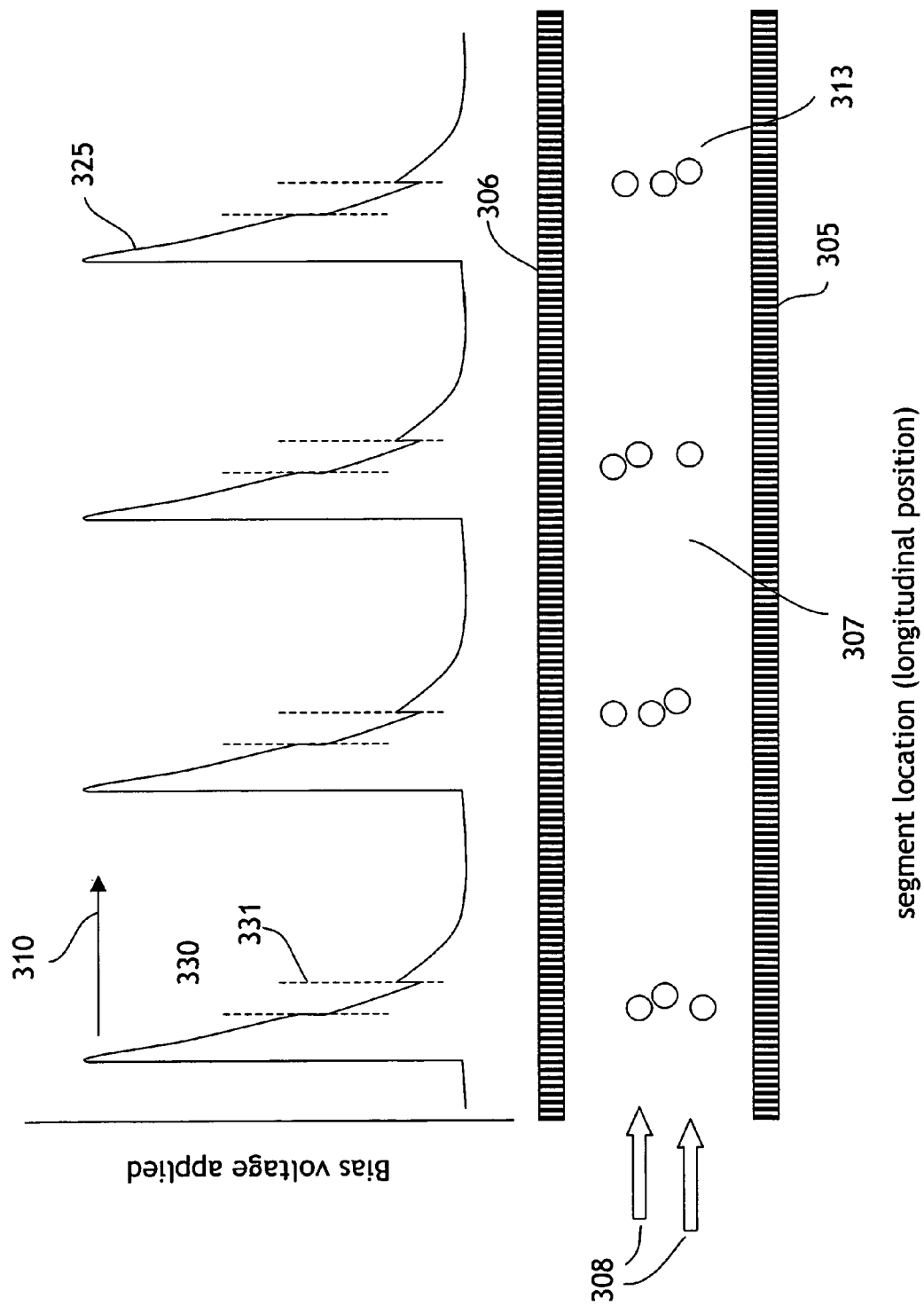
FIG. 6e illustrates a wider view of the repeating pattern of traveling dc bias voltages applied to the segmented outer electrode of FAIMS, and the distribution of ions in response to this applied pattern.

FIG. 6e illustrates a series of peaks in trace 325 that illustrates the voltages applied to the segments of the outer segmented-electrode 306. The voltages applied to the inner segmented-electrode are omitted for clarity. In each peak of the trace 325, a certain portion of the segments continue to provide a difference of voltage between the inner and outer cylinders of FAIMS equal to CV, and only the ions that are being transported at that condition of CV and slope of the trace 325 are transmitted to the not illustrated ion outlet of this FAIMS device. Optionally, the ions are further separated, by mass spectrometry, or detected by an electrometer as some non-limiting examples. In this case, the ion flow represents only ions with specific selected properties. For example the ions may be derived from an explosive compound, and the detection of these ions initiates further response to the presence of the compound. Because of the selectivity derived from the separation based on several properties of the ions, including their behavior at high-field, and their low-field mobility, and optionally by further properties including the mass-to-charge ratio of the ion, the likelihood of correct identification of the explosive compound is very high, and the possibility of falsely responding to another non-explosive compound is correspondingly very low.

Figure 8:
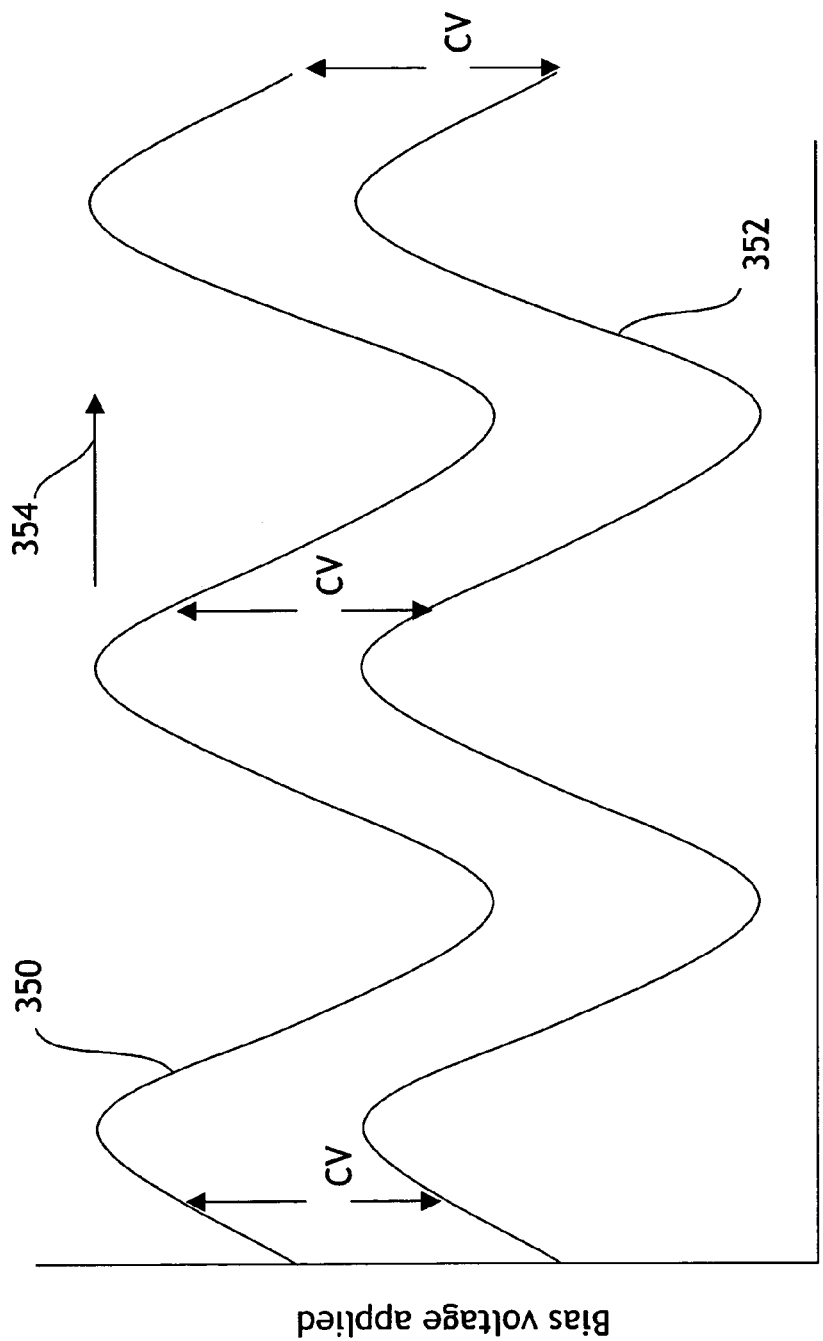
FIG. 8 illustrates traces representing the dc bias voltages applied to the segments of the inner and outer electrodes of segmented FAIMS, where the dc bias voltages are sinusoidal and are traveling longitudinally along the segments of the electrodes.

The segmented FAIMS is optionally operated with a traveling sinusoidal waveform shown in FIG. 8. The dc bias voltages applied to the outer electrode segments are shown as trace 350 and the dc bias voltages applied to the inner electrode segments are shown as trace 352. The waves are progressing from left to right in this figure at a velocity represented by arrow 354. At all locations the difference in the dc bias voltage applied to an outer segment and to the corresponding inner segment at the same longitudinal location differs by the compensation voltage, CV. Of course the asymmetric waveform is applied to all segments of one of the inner and outer segmented-electrodes. It is not immediately clear that an ion can be transported from left to right by the moving waves shown in FIG. 8, however the mechanism for transporting ions by this sinusoidal wave is analogous to the transport of a piece of wood by the waves in a lake. This mechanism is reviewed below, but is not intended to limit in any way the scope of the invention as defined by the appended claims.

Unlike the ion separation systems described in FIGS. 4 and 6, where a moving wavefront carries the ions on its rising crest in dependence on their low-field mobility, the sinusoidal moving waves shown in FIG. 8 require a gated pulse of ions in order to achieve separation in dependence of the low-field mobility of the ions. An optional mechanism for gating the flowing stream of ions is illustrated by the sequence of FIGS. 9a through 9d.

Figure 9A:
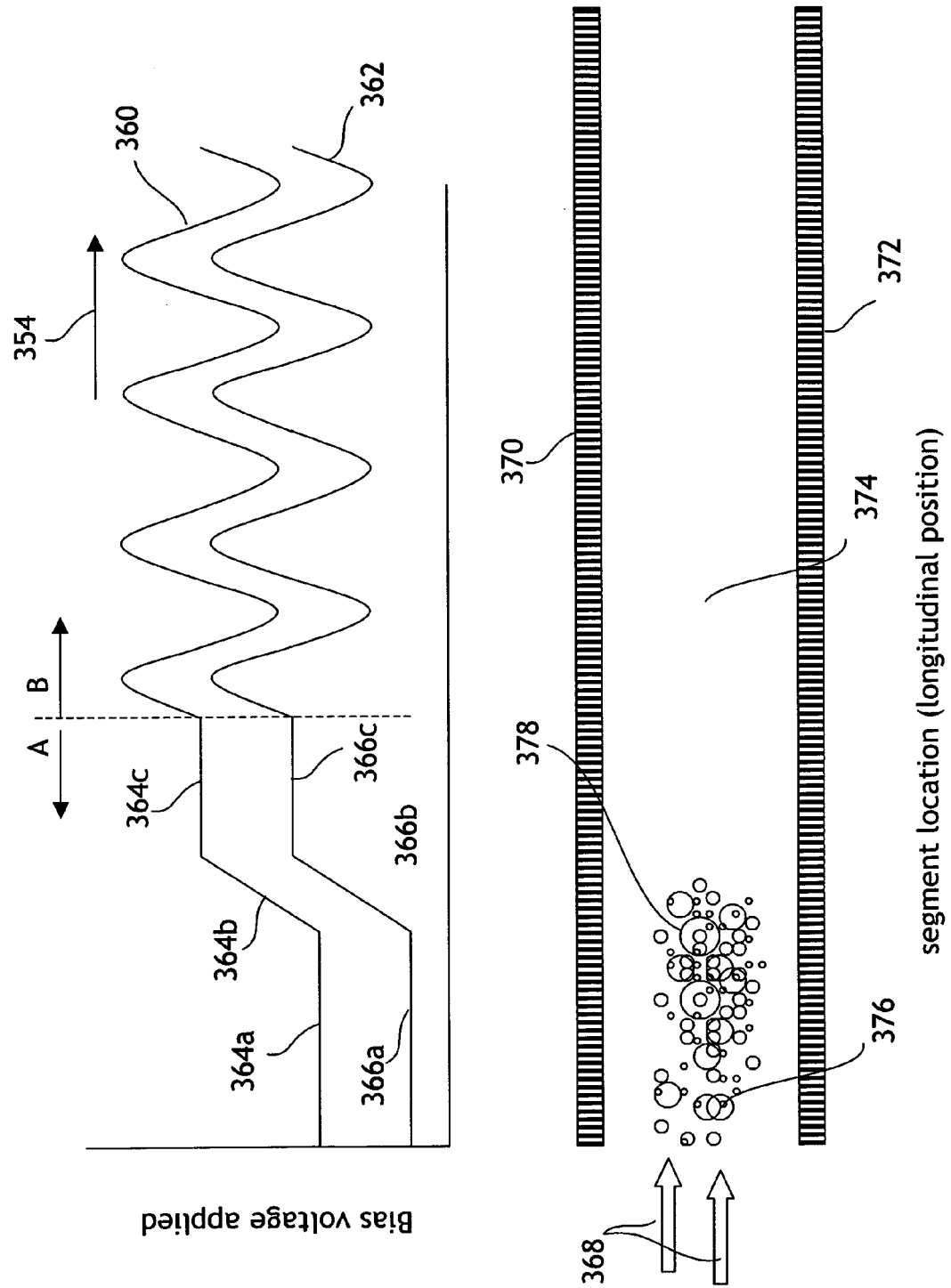
FIG. 9a illustrates a selected pattern of static dc bias voltages (gate closed) applied to a first portion of the segmented inner and outer electrode of FAIMS, and a sinusoidal shaped traveling pattern of dc bias voltages applied to a second portion of the segmented inner and outer electrodes of FAIMS, and the distribution of ions resulting from this pattern.

Referring to FIG. 9a, a continuous stream of a pre-selected mixture of ions 376 is flowing between the outer segmented-electrode 370 and the inner segmented-electrode 372. An optional flow of gas of velocity shown by the open arrows 368 is transporting the ions along the analyzer region 374. In a second, optional approach the ions are transported against the gas flow by superimposing a stream of peaks moving from left to right upon the dc bias voltages applied to the segments on the left half of FIG. 9a on the left side of the dashed line indicated by the letter A. The moving peaks act like a conveyor belt, and carry the ions against the flow of gas. For simplicity in discussion, FIG. 9a illustrates a flow of gas that is moving from left to right.

Still referring to FIG. 9a, the traces showing the dc bias voltages on the segmented electrodes is divided into two portions, by the dashed vertical line. The region to the left of the dashed line (indicated by A) corresponds to segments that are being used to gate a pulse of ions into the region to the right, and a region to the right of the dashed line (indicated by B) where the segment dc bias voltages are being changed in time to generate the appearance of a moving series of sinusoidal waves. In the region A, to the left of the dashed line, the applied dc bias voltages are not being translated along the segments, but remain applied constantly as shown. The mixture of ions 376 has previously been separated from some original more-complex mixture by being transported along a first region of the FAIMS where the segments are at constant voltages 364a and 366a in the upper traces showing the applied dc bias voltages. The applied asymmetric waveform (not shown) and the dc bias voltage difference between the segments (CV) are appropriate for transmission of one subset of ions shown as mixture of ions 376.

Figure 9B:
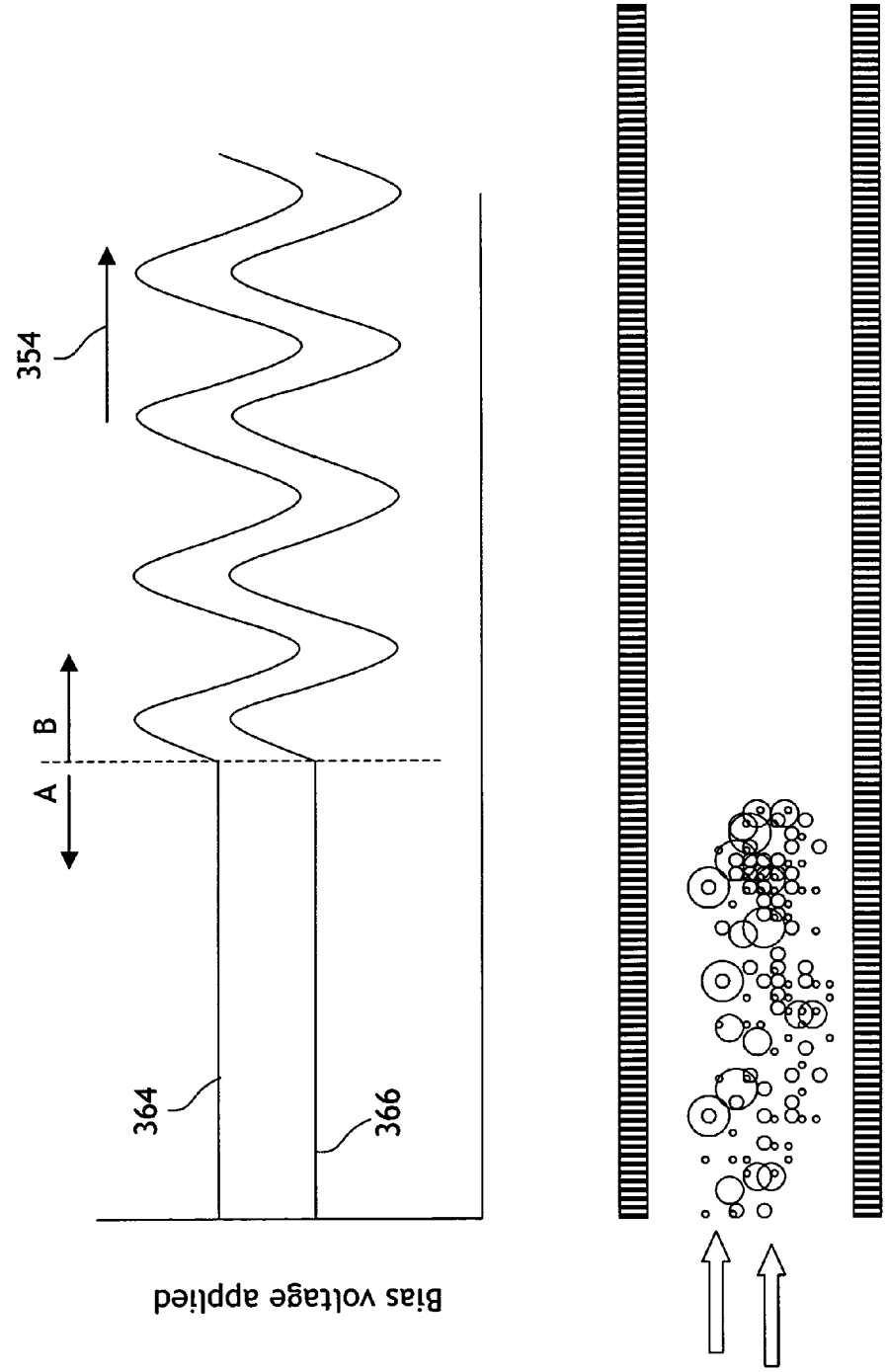
FIG. 9b illustrates a selected pattern of static dc bias voltages (gate opened) applied to a first portion of the segmented inner and outer electrode of FAIMS, and a sinusoidal shaped traveling pattern of dc bias voltages applied to a second portion of the segmented inner and outer electrodes of FAIMS, and the distribution of ions resulting from this pattern.

Still referring to FIG. 9a, the mixture of ions 376 is carried to a region where the dc bias voltages applied to the outer segments and inner segments is shown by trace 364b and 366b. As shown, the voltage difference between the inner and outer segments is CV but has a sharp potential rise for stopping the arriving ions. As a result of this potential barrier the ions are accumulating and being trapped between the electrodes in the region 378 of the lower half of FIG. 9a. Those ions, selected by the DV and CV conditions prior to segments 364b and 366b cannot be transmitted past the potential barrier by the stopping voltages applied to segments 364b and 366b. The region of segments shown by traces 364b and 366b may be operated as a gate for ion transmission. FIG. 9b is similar to FIG. 9a, but the dc bias voltages in the region indicated by traces 364b and 366b have been temporarily returned to a condition wherein the dc bias voltage between the inner and outer segments is equal to CV, and the packet of trapped ions is released and is transmitted through the region. In FIG. 9b the ion cloud has only begun to reach the segments where the sinusoidal waveforms are being applied.

Figure 9C:
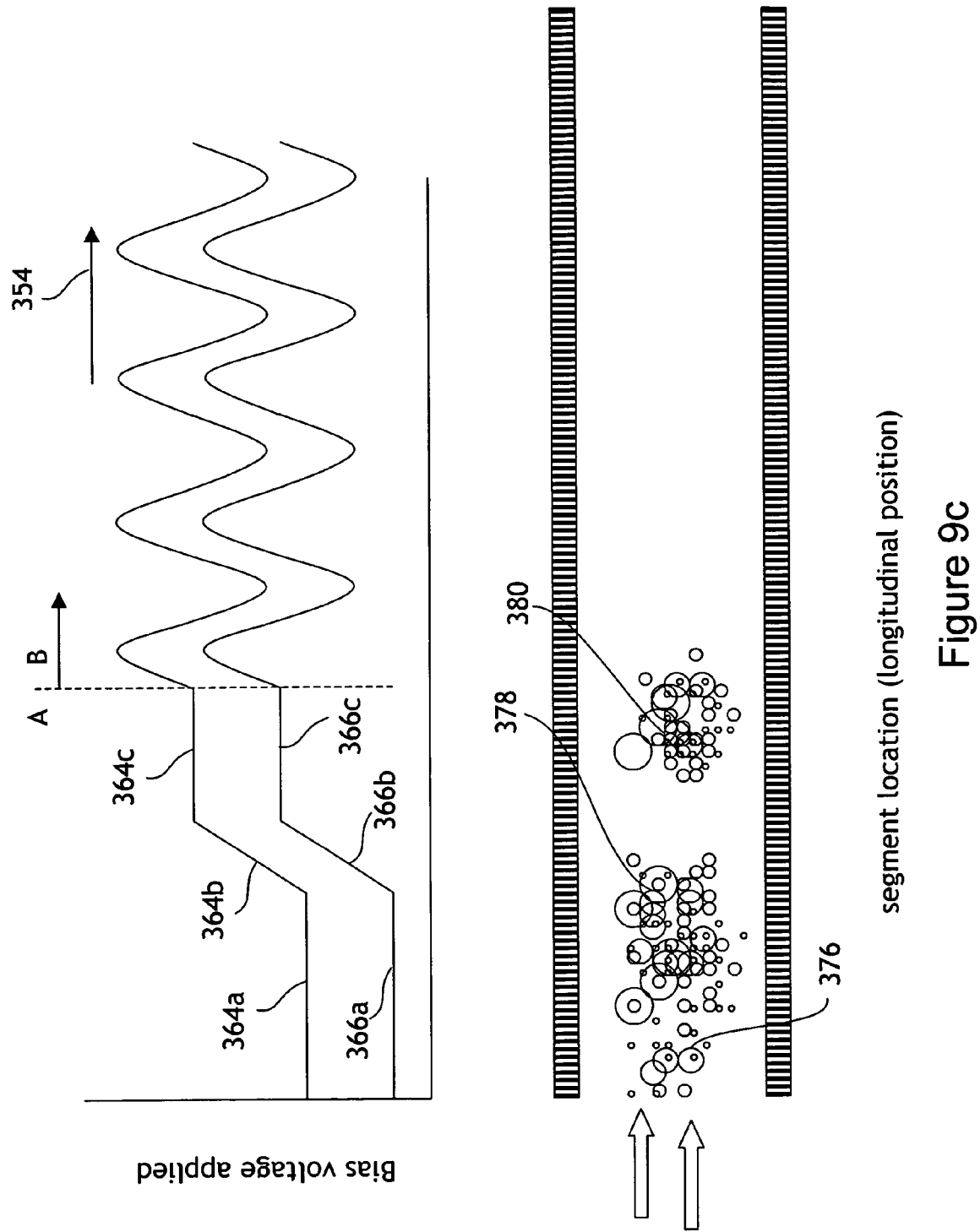
FIG. 9c illustrates a selected pattern of static dc bias voltages (gate closed) applied to a first portion of the segmented inner and outer electrode of FAIMS, and a sinusoidal shaped traveling pattern of dc bias voltages applied to a second portion of the segmented inner and outer electrodes of FAIMS, and the distribution of ions resulting from this pattern.

Referring to FIG. 9c, the voltages to the segments to the left of the dashed line in the upper traces has again been returned to equal to those shown in FIG. 9a. Again, the stream of ions 376 is trapped between the electrodes in region 378 because the dc bias voltages applied to the segments of the inner and outer electrodes have a stopping voltage, in other words a steep potential barrier. However, a previously trapped cluster of ions 380 has been transmitted during the portion of time indicated in FIG. 9b. Recall that this cluster of ions has already been pre-selected on the basis of their high-field mobility properties during transport at conditions of CV, DV, and other ambient conditions including gas composition, gas temperature and gas pressure as non-limiting examples.

Figure 9D:
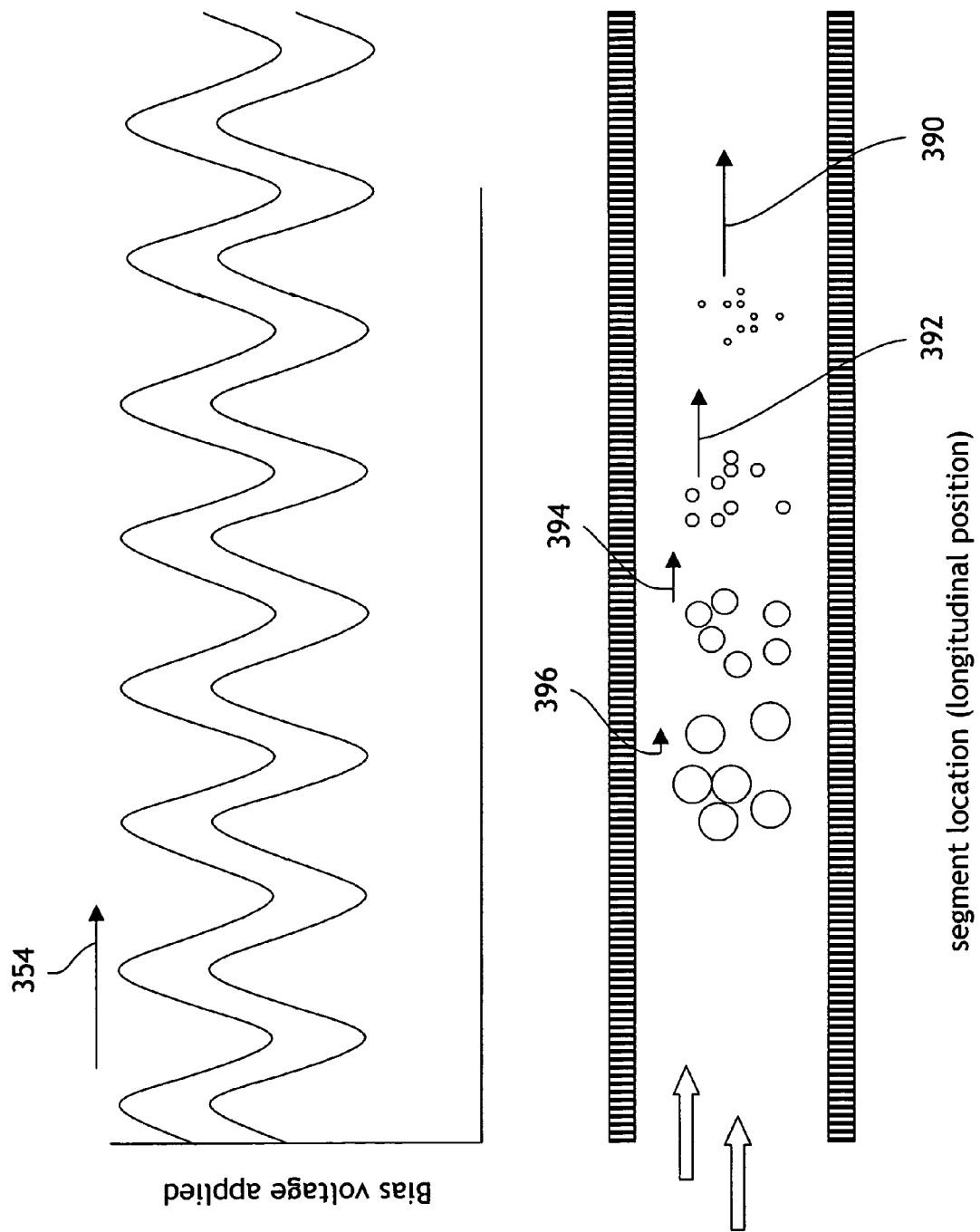
FIG. 9d illustrates a sinusoidal traveling pattern of dc bias voltages applied to a second portion of the segmented inner and outer electrodes of FAIMS, and the separation-in-space of ions based on their low-field mobility resulting from this pattern.

The cluster of ions 380 shown in FIG. 9c is carried by the flow of gas into the region of moving sinusoidal waves, shown by the region B to the right of the dashed line in the upper half of the figure. For simplicity the transition between static applied dc bias voltages in region A, and the traveling sinusoidal waves in region B has not been shown accurately in FIGS. 9a, 9b and 9c. FIG. 9d illustrates the separation of the ions that composed the cluster of ions 380 of FIG. 9c, at a later time as the ions are transported along the segmented electrodes. In this region of moving sinusoidal voltages applied to the electrodes, the ions are carried even absent a flow of gas. Moreover, the moving waveform may optionally be used to carry the ions against the flow of gas.

Still referring to FIG. 9d the ions are carried by the sinusoidal moving waves at velocities in respect to the low-field mobility of the ion, where velocity of the ions of low cross section is represented by the long arrow 390, the ions of intermediate mobility by arrows 392 and 394, and the ion of lowest mobility by arrow 396. This translation motion that occurs during passage of the sinusoidal waves occurs without contribution by the carrier gas, and the arrows 390, 392, 394 and 396 were drawn to indicate the longitudinal motion of the ions absent the flow of carrier gas.

Still referring to FIG. 9d, the ions that were in cluster 380 shown in FIG. 9c, are distributed in space according to their low-field mobility. This separation-in-space in dependence of low-field mobility is detected as time-of-flight when the ions arrive at the not illustrated ion outlet of FAIMS. It is important that the spatial distribution is not distorted as the ions are delivered to the ion outlet. The ions passing out of the ion outlet may be detected as they arrive in time at an electrometer detector, or by a mass spectrometer having suitable time-resolution detection, a TOF mass spectrometer as a non-limiting example.

Still referring to FIG. 9d, the ions are being separated by the same mechanism that causes a piece of wood to drift in a lake because of the passage of the waves. This drift is caused because when the object is being carried forward by the approaching wave, the velocity of the object is aligned with the motion of the wave. This velocity of the object in the same direction as the wave causes the object to spend an extended time in this forward pushing part of the wave. When the object rises to the top of the crest and begins to fall down the back side, the object starts to travel backwards, because it is now located on the backward facing part of the wave. It would appear, at first brush, that this process should be the exact reverse of the forward-pushing effect on the rising part of the wave. It would appear that the object should now move backward relative to the wave motion, and return to the starting location. This does not happen because when riding the back side of the wave, the object acquires a motion, and velocity in the direction opposite to the moving wave, and therefore this backward velocity causes the object to spend less time on the back side of the wave, than it did on the front side.

Still referring to FIG. 9d, the understanding of the motion of the ions caused by the sinusoidal moving waves is essential to selecting conditions wherein this separation operates. Clearly, if the wave voltages are too high, all of the ions will "surf" along the fronts, as they did in FIG. 4 and FIG. 6, and the type of separation shown in FIG. 9d does not occur. In other words, the longitudinal field generated by the sinusoidal shaped dc bias voltages applied to the segments should be sufficiently weak to allow the ions to ride up over the tops and move in the reverse direction on the back-side of the waves. This separation requires careful selection of the magnitude of the dc bias voltages and the selection of the longitudinal velocity of the sinusoidal waves, as indicated by the arrow 354 in FIG. 9d, these conditions selected in dependence of the expected low-field mobility of the types of ions being separated.

Figure 10:
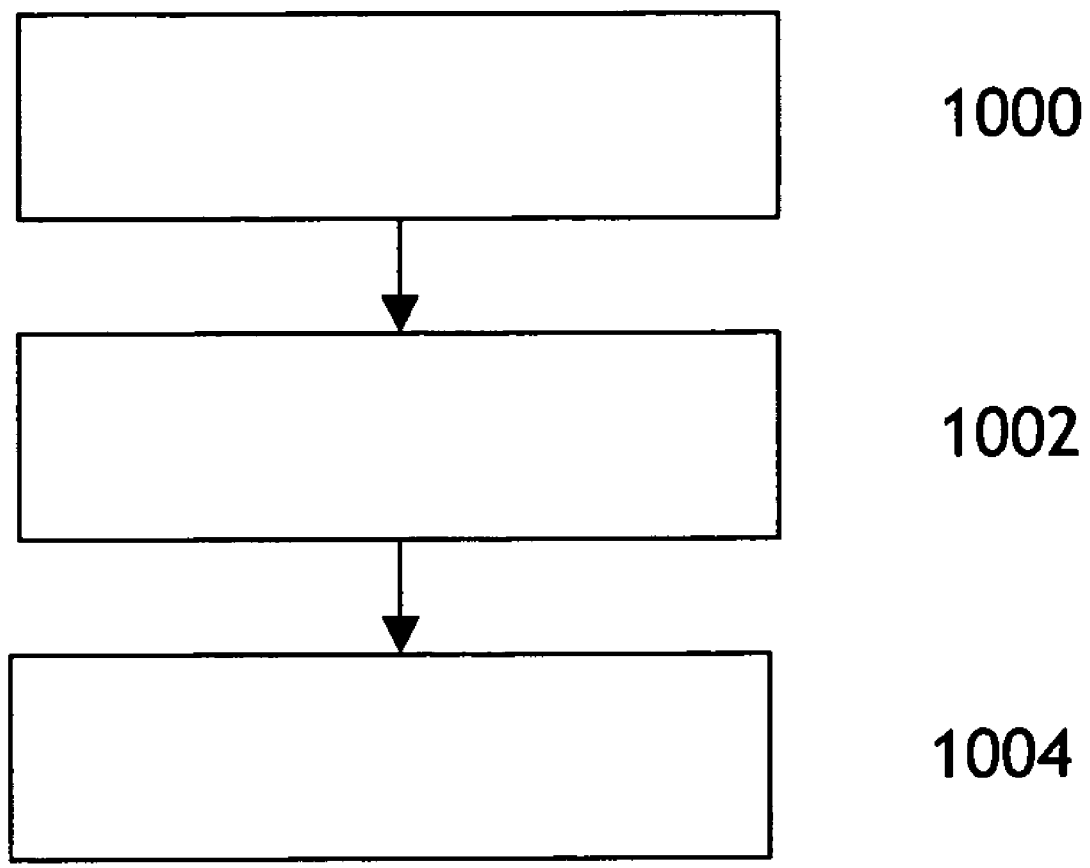
FIG. 10 is a simplified flow diagram of a method of separating ions according to the instant invention.

Referring now to FIG. 10, shown is a simplified flow diagram of a method of separating ions according to an embodiment of the instant invention. At step 1000, a segmented analyzer region is provided, the segmented analyzer region having an average ion flow path. Non-limiting examples include the analyzer region that was discussed with reference to either one of FIG. 1 and FIG. 7. During a period of time, an electrical field component is provided within the analyzer region at step 1002, the electrical field component being directed along a direction normal to the average ion flow path. The electrical field component directed along a direction normal to the average ion flow path is for selectively transmitting within the analyzer region ions having predetermined high field mobility properties, according to the FAIMS principle. During the same period of time, an electrical field component is providing within the segmented analyzer region at step 1004, the electrical field component being directed approximately along the average ion flow path, for at least partially separating the selectively transmitted ions in space along the average ion flow path in dependence upon the low field mobility properties of the selectively transmitted ions.

Optionally, the electrical field component directed approximately along the average ion flow path is of constant electric field strength as shown in either one of FIG. 1a and FIG. 1b. Further optionally, the electrical field component directed approximately along the average ion flow path is "static" and the electrical field strength one of increases and decreases, as shown for instance in FIG. 3. Still further optionally, the electrical field component directed approximately along the average ion flow path is a "traveling" waveform of the type shown in FIGS. 4a through 4c, and optionally the magnitude of the applied direct current bias voltage is increased gradually as shown in FIG. 6a. Further optionally, ions having the predetermined high field mobility properties are gated into the segmented analyzer region, and the electrical field component directed approximately along the average ion flow path is in the form of a "traveling" sinusoidal waveform, as is shown in FIG. 8.

Figure 11:
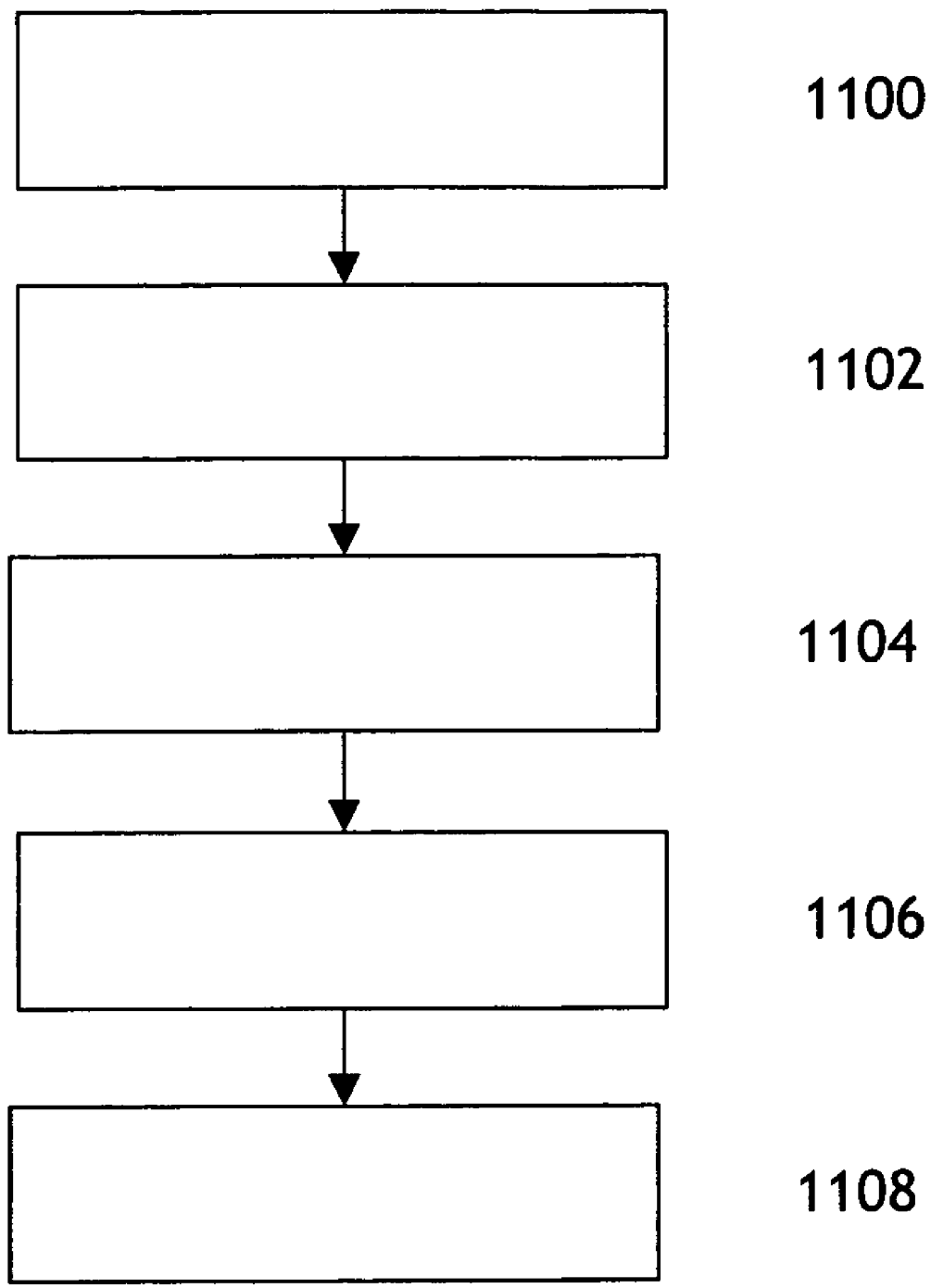
FIG. 11 is a simplified flow diagram of another method of separating ions according to the instant invention.

Referring now to FIG. 11, shown is a simplified flow diagram of another method of separating ions according to an embodiment of the instant invention. At step 1100 an analyzer region having an average ion flow path providing is provided, the analyzer region being defined by a space between facing electrode surfaces of a plurality of electrode segment pairs. Non-limiting examples include the analyzer region that was discussed with reference to either one of FIG. 1 and FIG. 7. At step 1102 ions are introduced from an ionization source into the analyzer region. At step 1104, an asymmetric waveform voltage is applied to at least one electrode segment of each of the plurality of electrode segment pairs, and a direct current voltage difference is applied between the facing electrode surfaces of each electrode segment pair, to establish an electrical field for selectively transmitting within the analyzer region a subset of the ions having predetermined high field mobility properties. At step 1006, a direct current voltage difference is applied between adjacent electrode segment pairs of the plurality of electrode segment pairs, to establish an electric field along the average ion flow path for at least partially separating the subset of the ions in space along the average ion flow path in dependence upon the low field mobility properties of the subset of the ions. At step 1008, the direct current voltage difference that is applied between the facing electrode surfaces of some of the electrode segment pairs is changed to a value that is not suitable for selectively transmitting ions within the analyzer region between the facing electrode surfaces of those electrode segment pairs. Accordingly, a type of ion having predetermined high field and low field mobility properties is transmitted with very high selectivity.

Optionally, the electrical field component directed approximately along the average ion flow path is of constant electric field strength as shown in either one of FIG. 1a and FIG. 1b. Further optionally, the electrical field component directed approximately along the average ion flow path is "static" and the electrical field strength one of increases and decreases, as shown for instance in FIG. 3. Still further optionally, the electrical field component directed approximately along the average ion flow path is a "traveling" waveform of the type shown in FIGS. 4a through 4c, and optionally the magnitude of the applied direct current bias voltage is increased gradually as shown in FIG. 6a. By way of a non-limiting example, the step 1008 of changing the direct current voltage difference is performed in a manner substantially as illustrated in FIG. 6c. The "some" of the electrode segment pairs optionally includes the electrode segment pairs in the region indicated by dashed line a, c and/or d. Optionally, the dc bias voltage applied to one electrode segment of an electrode segment pair is changed. Further optionally, the dc bias voltages applied to both electrode segments of an electrode segment pair are changed, but in a manner resulting in a dc voltage difference between the electrode segments of the pair that does not support ion transmission.

Figure 12:
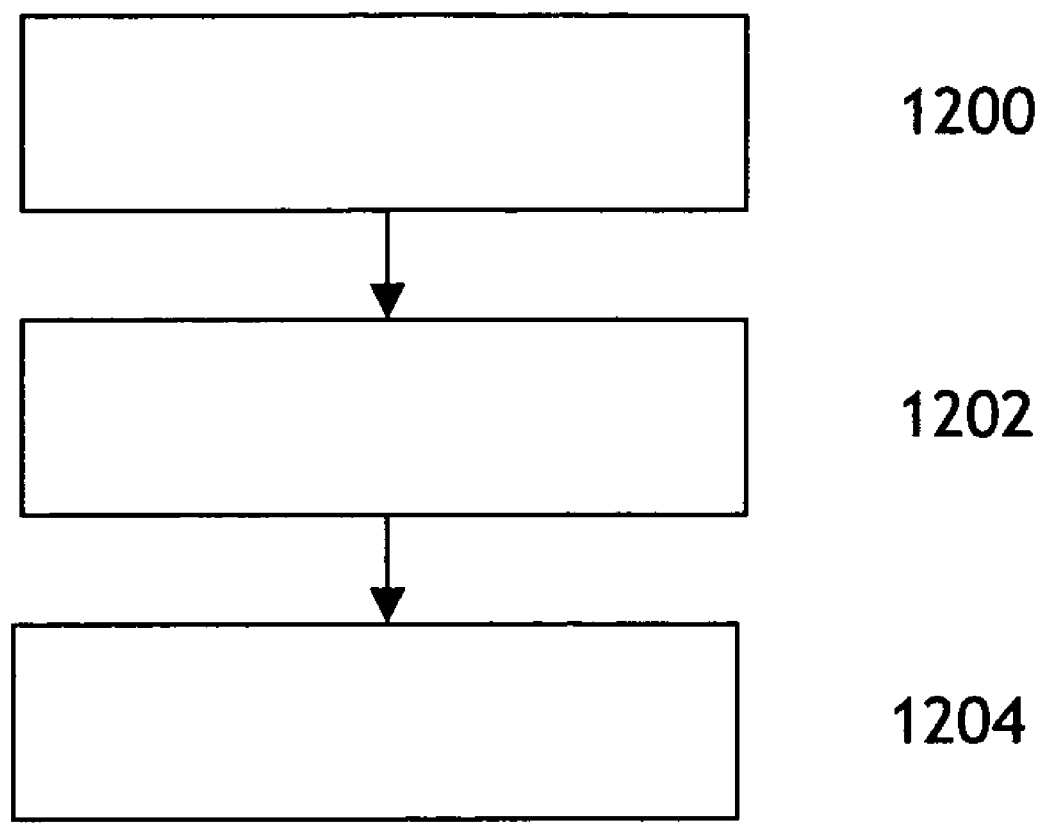
FIG. 12 is a simplified flow diagram of another method of separating ions according to the instant invention; and, FIG. 13 is a simplified flow diagram of another method of separating ions according to the instant invention.

Referring now to FIG. 12, shown is a simplified flow diagram of another method of separating ions according to an embodiment of the instant invention. At step 1200 a segmented analyzer region having an average ion flow path is provided. During a period of time, an electrical field component is provided within the segmented analyzer region at step 1202, the electric field component being directed along a direction normal to the average ion flow path. The electric field component directed along a direction normal to the average ion flow path is for selectively transmitting within the segmented analyzer region ions having predetermined high field mobility properties. During the period of time, an electrical field component is provided within the segmented analyzer region at step 1204, the electric field component being directed along the average ion flow path and having an electrical field strength that varies along the average ion flow path. The electric field component directed along the average ion flow path is for at least partially separating the selectively transmitted ions in space along the average ion flow path, in dependence upon the low field mobility properties of the selectively transmitted ions.

Optionally, the electrical field component directed approximately along the average ion flow path is "static" and the electric field strength one of increases and decreases, as shown for instance in FIG. 3. Further optionally, the electrical field component directed approximately along the average ion flow path is a "traveling" waveform of the type shown in FIG. 4a through 4c, and optionally the magnitude of the applied direct current bias voltage is increased gradually as shown in FIG. 6a. Still further optionally, ions having the predetermined high field mobility properties are gated into the segmented analyzer region, and the electrical field component directed approximately along the average ion flow path is in the form of a "traveling" sinusoidal waveform, as is shown in FIG. 8.

Figure 13:
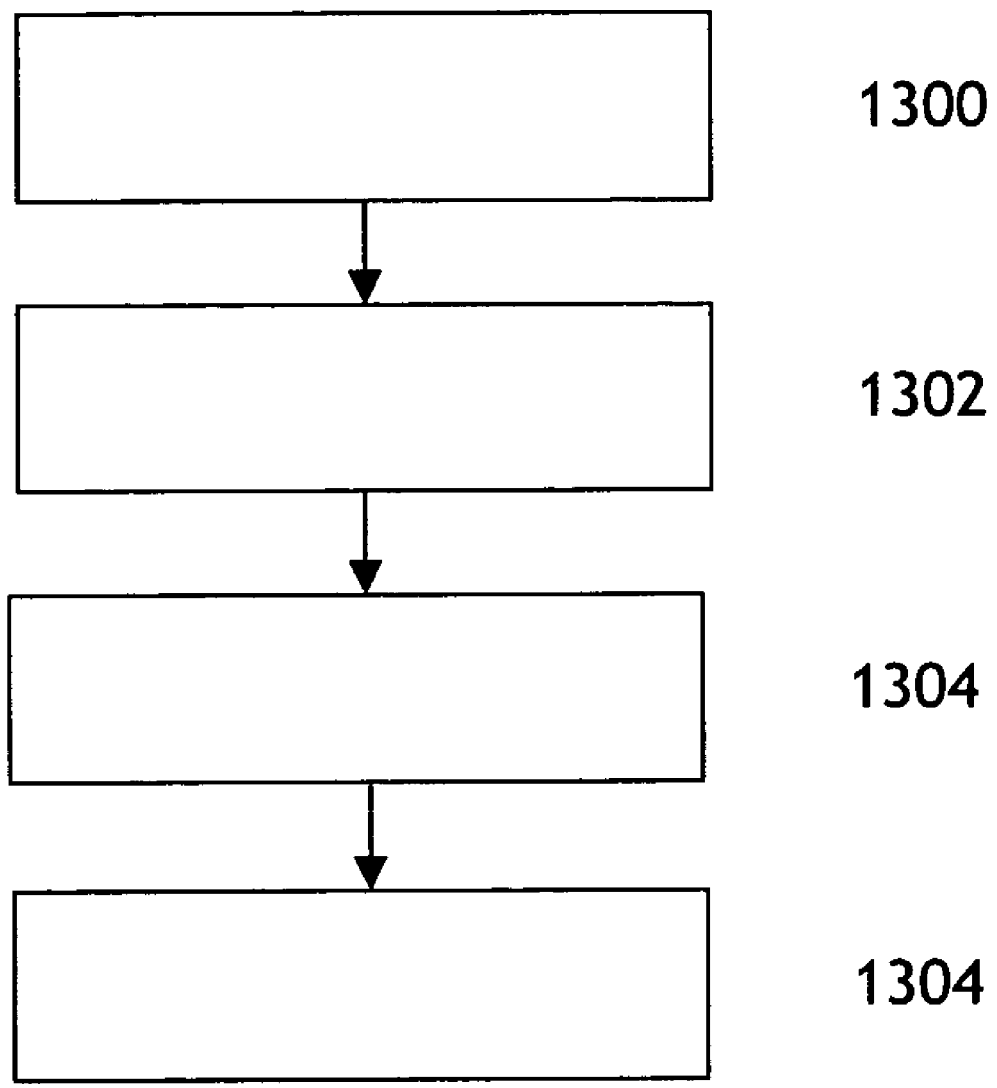

Referring now to FIG. 13, shown is a simplified flow diagram of a method of separating ions according to an embodiment of the instant invention. At step 1300, an analyzer region having an average ion flow path is provided, the analyzer region defined by a space between facing electrode surfaces of a plurality of electrode segment pairs including n segment pairs. Non-limiting examples include the analyzer region that was discussed with reference to either one of FIG. 1 and FIG. 7. During a period of time, at step 1302 an asymmetric waveform voltage is applied to each electrode segment pair of the plurality of electrode segment pairs and a direct current voltage difference is applied between the facing electrode surfaces of each electrode segment pair. In this way, an electrical field is established for selectively transmitting within the analyzer region a subset of the ions having predetermined high field mobility properties. During a first portion of the period of time, at step 1304 a different dc bias voltage relative to a reference voltage is applied to each electrode segment pair. The different dc bias voltages are applied such that in a direction taken along the average ion flow path, the applied dc bias voltage one of increases and decreases from one electrode segment pair to an adjacent electrode segment pair between a first electrode segment pair and the $n^{th}$ electrode segment pair. During a second portion of the period of time not overlapping the first portion, at step 1306 a dc bias voltage corresponding to a dc bias voltage that was applied to an adjacent electrode segment pair during the first portion of the period of time is applied to each electrode segment pair. The application of dc bias voltages during the first portion of the period of time and during the second portion of the period of time cooperate to form a dc bias voltage wavefront that translates along the length of the analyzer region. This was shown previously with reference to FIGS. 4a-4c, and FIGS. 6a to 6d. Advantageously, the selectively transmitted ions are at least partially separated in space along the wavefront in dependence upon their low field mobility properties.

The segmented FAIMS with stationary or moving longitudinal fields considerably simplifies the ion transmission pathway relative to tandem-in-space hybrids in which the ions separated by FAIMS are coupled into the inlet of a conventional drift tube ion mobility spectrometer. The coupling of two systems together to get a separation based on FAIMS as well as a tandem in space separation based on low-field mobility suffers from ion losses in the transfer between systems. Although the mechanical assembly and the electronic control of a segmented FAIMS is complex, the ion pathway is very simple, and results in high ion transmission efficiency. The ions are separated both on FAIMS and low-field mobility properties within a single device. An embodiment of the invention is shown to combine the measurements relating to the FAIMS separation and the conventional drift tube ion mobility spectrometer into one instrument.

Generally, for a particular type of ion the high-field ion mobility properties used by FAIMS may not be related in a simple manner to the low-field ion mobility properties, therefore the separation of ions based on both ionic properties has superior specificity to either taken alone. Separations based on the present invention are faster than condensed phase separations such as liquid chromatography or electrophoresis, and the additional specificity of combined FAIMS and low-field mobility reduces the number of types of separations that require the slower condensed phase methods.

Use of cylindrical FAIMS electrodes provides high ion transmission efficiency. Conventional drift ion mobility spectrometers for low-field ion mobility measurements are generally characterized by an ion cloud that disperses in space, and this cloud of ions is difficult to transfer efficiently into a mass spectrometer. Similarly, those FAIMS systems based on flat parallel plates lack focusing and the ions are continuously lost to the electrodes, requiring fast ion transit times to minimize ion loss. If ion separation requires time, this additional required time is associated with further ion loss through diffusion and ion-ion mutual repulsion. It is an advantage of FAIMS that the ions can be confined in space in both 2-dimensions and 3-dimensions to avoid collisions with the electrode surfaces. Although a separation may require time, the ion loss is minimized.

The ions are often provided to FAIMS in a continuous stream from an ionization source. If FAIMS is designed to accept the ions continuously, this beneficially eliminates the need for ion gating to provide pulses of ions at specific windows of time, as is required in conventional drift tube ion mobility spectrometers. Acceptance of a continuous stream of ions minimizes ion loss. Conventional drift tube ion mobility spectrometry typically employs ion gates to introduce ions into a tube through which the ions drift. Arrival times at the end of the drift reflect the drift velocity, hence the low-field ion mobility of the various types of ions. This time-of-flight system is limited because the ions are only introduced to the flight tube intermittently, with concomitant reduction of duty cycle. One embodiment of the invention described here permits continuous acceptance of a flowing stream of ions, and selecting a subset of the stream of ions based both on high-field mobility and the low-field mobility properties of the ions. The ions may be transmitted out of FAIMS in a time-dependent fashion related to their low-field mobility, or a selected ion may be transmitted after removal of ions with other than the selected low field mobility.

This invention describes a means for gating a continuous stream of ions using segmented FAIMS. All ions are pre-separated by FAIMS. A time-limited portion of ions can be gated using segmented FAIMS, by controlling a stopping voltage within certain parts of the segmented FAIMS. In this way, the present invention illustrates that a packet of ions can be isolated and trapped prior to release for separation using a time-of-flight system based on a transport by sinusoidal waves traveling along the length of a segmented FAIMS. Separation using this mechanism in a cylindrical geometry FAIMS is highly efficient because of the focusing mechanism that helps minimize the collisions of the ions with the electrode walls.

Numerous other embodiments may be envisaged without departing from the spirit and scope of the invention.

What is claimed is:

1. A method of separating ions, comprising:
   providing a segmented analyzer region having an average ion flow path;
   during a period of time, providing within the analyzer region an electrical field component that is directed along a direction normal to the average ion flow path, for selectively transmitting within the analyzer region ions having predetermined high field mobility properties; and,
   during the period of time, providing within the segmented analyzer region an electrical field component that is directed approximately along the average ion flow path, for at least partially separating the selectively transmitted ions in space along the average ion flow path in dependence upon the low field mobility properties of the selectively transmitted ions.

2. A method of separating ions according to claim 1, wherein the strength of the electrical field component that is directed approximately along the average ion flow path one of increases and decreases along the average ion flow path.

3. A method of separating ions according to claim 1, wherein the strength of the electrical field component that is directed approximately along the average ion flow path is approximately constant along the average ion flow path.

4. A method of separating ions according to claim 1, wherein the electrical field component that is directed approximately along the average ion flow path comprises a train of repeating voltage waveforms, the electrical field strength one of increasing and decreasing smoothly along each one of the train of repeating voltage waveforms.

5. A method of separating ions according to claim 4, comprising translating the train of repeating voltage waveforms along a direction of the average ion flow path during the period of time.

6. A method of separating ions according to claim 1, wherein the electrical field component that is directed approximately along the average ion flow path comprises a train of sinusoidally varying repeating voltage waveforms.

7. A method of separating ions according to claim 6, comprising prior to the period of time, gating ions having the predetermined high field mobility properties into the segmented analyzer region.

8. A method of separating ions according to claim 1, comprising subsequent to the period of time, changing the electrical field component that is directed approximately along the average ion flow path for supporting extraction of the at least partially separated selectively transmitted ions in an order relating to the low field mobility properties of the ions.

9. A method of separating ions according to claim 1, comprising subsequent to the period of time, providing within a portion of the segmented analyzer region electrical field conditions that are unsuitable for selectively transmitting ions contained within said portion.

10. A method of separating ions according to claim 8, comprising selectively transmitting ions contained within other than the portion of the segmented analyzer region along the average ion flow path and out through an ion outlet of the segmented analyzer region.

11. A method of separating ions according to claim 1, comprising providing a flow of a carrier gas within the segmented analyzer region during the period of time.

12. A method of separating ions according to claim 1, comprising prior to the period of time:
   introducing ions into a portion of the segmented analyzer region; and,
   providing within the portion of the segmented analyzer region an electrical field that is directed along a direction normal to the average ion flow path, for selectively transmitting within the portion of the segmented analyzer region ions having the predetermined high field mobility properties.

13. A method of separating ions, comprising:
   providing an analyzer region having an average ion flow path, the analyzer region defined by a space between facing electrode surfaces of a plurality of electrode segment pairs;
   introducing ions from an ionization source into the analyzer region;
   applying an asymmetric waveform voltage to at least one electrode segment of each of the plurality of electrode segment pairs and applying a direct current voltage difference between the facing electrode surfaces of each electrode segment pair, to establish an electrical field for selectively transmitting within the analyzer region a subset of the ions having predetermined high field mobility properties;
   applying a direct current voltage difference between adjacent electrode segment pairs of the plurality of electrode segment pairs, to establish an electric field along the average ion flow path for at least partially separating the subset of the ions in space along the average ion flow path in dependence upon the low field mobility properties of the subset of the ions; and,
   changing the direct current voltage difference that is applied between the facing electrode surfaces of some of the electrode segment pairs to a value that is not suitable for selectively transmitting ions within the analyzer region between the facing electrode surfaces of the some of the electrode segment pairs, so as to preferentially transmit a type of ion having predetermined high field and low field mobility properties.

14. A method of separating ions according to claim 13, wherein a magnitude of the direct current voltage difference between adjacent electrode segment pairs is approximately constant along the average ion flow path.

15. A method of separating ions according to claim 13, wherein a magnitude of the direct current voltage difference between adjacent electrode segment pairs one of increases and decreases along the average ion flow path.

16. A method of separating ions according to claim 13, wherein a magnitude of the direct current voltage difference between adjacent electrode segment pairs varies in a repeating manner along the average ion flow path.

17. A method of separating ions according to claim 13, wherein a magnitude of the direct current voltage difference between adjacent electrode segment pairs one of increases and decreases along a first portion of the plurality of electrode segment pairs at a first instantaneous point in time.

18. A method of separating ions according to claim 13, wherein a magnitude of the direct current voltage difference between adjacent electrode segment pairs one of increases and decreases discontinuously so as to form a train of repeating voltage waveforms along the average ion flow path at a first instantaneous point in time.

19. A method of separating ions according to claim 13, comprising selectively transmitting the type of ion having predetermined high field and low field mobility properties along the average ion flow path and out through an ion outlet of the analyzer region.

20. A method of separating ions according to claim 13, comprising providing a flow of a carrier gas within the analyzer region.

21. A method of separating ions, comprising:
   providing a segmented analyzer region having an average ion flow path;
   during a period of time, providing within the segmented analyzer region an electrical field component that is directed along a direction normal to the average ion flow path, for selectively transmitting within the segmented analyzer region ions having predetermined high field mobility properties; and,
   during the period of time, providing within the segmented analyzer region an electrical field component that is directed along the average ion flow path and having an electrical field strength that varies along the average ion flow path, for at least partially separating the selectively transmitted ions in space along the average ion flow path in dependence upon the low field mobility properties of the selectively transmitted ions.

22. A method of separating ions according to claim 21, wherein the segmented analyzer region is defined by a space between facing electrode surfaces of a plurality of electrode segment pairs and comprising applying an asymmetric waveform voltage to at least one electrode segment of each of the plurality of electrode segment pairs and applying a direct current voltage difference between the facing electrode surfaces of each electrode segment pair, so as to provide the electrical field component that is directed along a direction normal to the average ion flow path.

23. A method of separating ions according to claim 22, comprising applying a direct current voltage difference between adjacent electrode segment pairs of the plurality of electrode segment pairs, a magnitude of the direct current voltage difference between adjacent electrode segment pairs one of increasing and decreasing in a direction along the average ion flow path, so as to provide the electrical field component that is directed along the average ion flow path.

24. A method of separating ions according to claim 23, comprising changing the direct current voltage difference that is applied between the facing electrode surfaces of some of the electrode segment pairs to a value that is not suitable for selectively transmitting ions within the segmented analyzer region between the facing electrode surfaces of the some of the electrode segment pairs, so as to preferentially transmit a type of ion having predetermined high field and low field mobility properties.

25. A method of separating ions according to claim 24, comprising selectively transmitting the type of ion having predetermined high field and low field mobility properties along the average ion flow path and out through an ion outlet of the segmented analyzer region.

26. A method of separating ions according to claim 21, comprising providing a flow of a carrier gas within the segmented analyzer region.

27. A method of separating ions, comprising:
providing an analyzer region having an average ion flow path, the analyzer region defined by a space between facing electrode surfaces of a plurality of electrode segment pairs including n segment pairs;
during a period of time, applying an asymmetric waveform voltage to each electrode segment pair of the plurality of electrode segment pairs and applying a direct current voltage difference between the facing electrode surfaces of each electrode segment pair, to establish an electrical field for selectively transmitting within the analyzer region a subset of the ions having predetermined high field mobility properties;
during a first portion of the period of time, applying to each electrode segment pair a different dc bias voltage relative to a reference voltage, such that in a direction taken along the average ion flow path the applied dc bias voltage one of increases and decreases from one electrode segment pair to an adjacent electrode segment pair between a first electrode segment pair and the $n^{th}$ electrode segment pair; and,
during a second portion of the period of time not overlapping the first portion, applying to each electrode segment pair a dc bias voltage corresponding to a dc bias voltage that was applied to an adjacent electrode segment pair during the first portion of the period of time,
wherein the application of dc bias voltages during the first portion of the period of time and during the second portion of the period of time cooperate to form a dc bias voltage wavefront that translates along the length of the analyzer region, and wherein the selectively transmitted ions are at least partially separated in space along the wavefront in dependence upon their low field mobility properties.

28. A method of separating ions according to claim 27, comprising providing a flow of a carrier gas within the analyzer region during the period of time.

29. A method of separating ions according to claim 27, comprising prior to the period of time:
introducing ions into a portion of the analyzer region; and,
providing within the portion of the analyzer region an electrical field that is directed along a direction normal to the average ion flow path, for selectively transmitting within the portion of the analyzer region ions having the predetermined high field mobility properties.

30. A method of separating ions according to claim 27, comprising subsequent to the period of time, applying a direct current voltage difference between the facing electrode surfaces of a subset of the plurality of electrode segment pairs, so as to establish an electrical field that is unsuitable for selectively transmitting ions that are located within a portion of the analyzer region that is defined between the facing electrode surfaces of said subset of the plurality of the electrode segment pairs.

31. A method of separating ions according to claim 30, comprising selectively transmitting ions contained within other than the portion of the analyzer region along the average ion flow path and out through an ion outlet of the analyzer region.

* * * * *